(12) United States Patent
Andersson et al.

(10) Patent No.: US 10,142,746 B2
(45) Date of Patent: Nov. 27, 2018

(54) HEARING PROSTHESIS WITH A PIEZOELECTRIC ACTUATOR

(71) Applicant: Cochlear Limited, Macquarie University, NSW (AU)

(72) Inventors: Marcus Andersson, Gothenburg (SE); Bart Valckaerts, Borgerhout (BE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 14/822,333

(22) Filed: Aug. 10, 2015

(65) Prior Publication Data

US 2016/0037274 A1 Feb. 4, 2016

Related U.S. Application Data

(63) Continuation of application No. 13/078,402, filed on Apr. 1, 2011, now Pat. No. 9,107,013.

(51) Int. Cl.
*H04R 25/00* (2006.01)
*H04R 17/00* (2006.01)
*A61F 11/04* (2006.01)

(52) U.S. Cl.
CPC .......... *H04R 25/606* (2013.01); *A61F 11/045* (2013.01); *H04R 17/00* (2013.01); *H04R 25/604* (2013.01); *H04R 25/554* (2013.01); *H04R 2460/13* (2013.01)

(58) Field of Classification Search
CPC ........ A61F 11/04; A61F 11/045; H04R 17/00; H04R 17/02; H04R 17/025; H04R 2460/13; H04R 25/60; H04R 25/604; H04R 25/606; H04R 25/00–25/75; H04R 17/005–17/10; H04R 2460/00–2460/17
See application file for complete search history.

(56) References Cited

U.S. PATENT DOCUMENTS

| | | | |
|---|---|---|---|
| 2,045,403 A | 6/1936 | Nicholides |
| 2,045,404 A | 6/1936 | Nicholides |
| 2,045,427 A | 6/1936 | White |
| 2,239,550 A | 4/1941 | Cubert |
| 3,594,514 A | 7/1971 | Wingrove |

(Continued)

FOREIGN PATENT DOCUMENTS

| DE | 19643180 A1 | 4/1997 |
|---|---|---|
| JP | 59178986 A | 10/1984 |

(Continued)

OTHER PUBLICATIONS

"New 'extralibral' composite 'stiffer than diamond'", Materials World Magazine, Apr. 1, 2007, retrieved on Jun. 3, 2014 at http://www.iom3.org/news/new-extralibral-composite-stiffer-diamond?c=574.

(Continued)

*Primary Examiner* — Thaddeus Cox

(74) *Attorney, Agent, or Firm* — Pilloff & Passino LLP; Martin J. Cosenza

(57) ABSTRACT

A hearing prosthesis including an actuator. The actuator includes a material that deforms in response to an electrical signal and that is adapted to, upon implantation in a recipient, transmit vibrations representative of a sound signal to an organ of the recipient, wherein the material is at least partially exposed to at least one of body tissue and fluid of the recipient.

25 Claims, 18 Drawing Sheets

(56) References Cited

U.S. PATENT DOCUMENTS

| | | | |
|---|---|---|---|
| 4,498,461 A | 2/1985 | Håkansson | |
| 4,612,915 A | 9/1986 | Hough et al. | |
| 4,904,233 A | 2/1990 | Håkansson et al. | |
| 4,937,489 A | 6/1990 | Hattori et al. | |
| 4,952,835 A | 8/1990 | Stahlhuth | |
| 4,964,106 A | 10/1990 | Bromfield | |
| 5,228,092 A | 7/1993 | Nakamura et al. | |
| 5,245,245 A | 9/1993 | Goldenberg | |
| 5,286,199 A | 2/1994 | Kipke | |
| 5,344,387 A * | 9/1994 | Lupin | H04R 25/606 181/130 |
| 5,444,324 A | 8/1995 | Priest et al. | |
| 5,589,725 A | 12/1996 | Haertling | |
| 5,772,575 A | 6/1998 | Lesinski et al. | |
| 5,788,711 A | 8/1998 | Lehner et al. | |
| 5,800,536 A * | 9/1998 | Fisher | A61N 1/36036 607/116 |
| 5,899,847 A * | 5/1999 | Adams | A61N 1/36032 600/25 |
| 5,956,292 A * | 9/1999 | Bernstein | H04R 17/00 29/25.35 |
| 5,997,466 A * | 12/1999 | Adams | H04R 25/606 600/25 |
| 6,273,681 B1 | 8/2001 | Yamakawa et al. | |
| 6,294,859 B1 | 9/2001 | Jaenker | |
| 6,308,101 B1 | 10/2001 | Faltys et al. | |
| 6,371,415 B1 | 4/2002 | Lorkowski et al. | |
| 6,411,009 B2 | 6/2002 | Jaenker | |
| 6,463,157 B1 | 10/2002 | May | |
| 6,554,761 B1 | 4/2003 | Puria et al. | |
| 6,565,503 B2 | 5/2003 | Leysieffer et al. | |
| 6,629,922 B1 | 10/2003 | Puria et al. | |
| 6,631,197 B1 | 10/2003 | Taenzer | |
| 6,751,334 B2 | 6/2004 | Håkansson | |
| 6,927,528 B2 | 8/2005 | Barillot et al. | |
| 6,994,110 B2 | 2/2006 | Barillot et al. | |
| 7,026,746 B2 | 4/2006 | Audren et al. | |
| 7,045,932 B2 | 5/2006 | Xu et al. | |
| 7,126,257 B2 | 10/2006 | Kampe et al. | |
| 7,224,815 B2 | 5/2007 | Maltan et al. | |
| 7,378,783 B2 | 5/2008 | Pelrine et al. | |
| 7,488,284 B2 | 2/2009 | Hanson et al. | |
| 7,564,988 B2 | 7/2009 | Azima et al. | |
| 7,722,524 B2 | 5/2010 | Lupin et al. | |
| 2001/0031908 A1 * | 10/2001 | Buschek | H04R 25/606 600/25 |
| 2002/0039427 A1 | 4/2002 | Whitwell et al. | |
| 2003/0137218 A1 | 7/2003 | Hermle et al. | |
| 2003/0151524 A1 * | 8/2003 | Clark | A61B 5/0031 340/870.07 |
| 2005/0020873 A1 | 1/2005 | Berrang et al. | |
| 2005/0090705 A1 | 4/2005 | Cho | |
| 2005/0163333 A1 | 7/2005 | Abel et al. | |
| 2006/0023908 A1 | 2/2006 | Perkins et al. | |
| 2006/0025648 A1 | 2/2006 | Lupin et al. | |
| 2006/0087203 A1 | 4/2006 | Cho | |
| 2007/0041595 A1 | 2/2007 | Carazo et al. | |
| 2007/0156011 A1 | 7/2007 | Westerkull | |
| 2007/0191673 A1 | 8/2007 | Ball et al. | |
| 2009/0052698 A1 | 2/2009 | Rader et al. | |
| 2009/0115292 A1 | 5/2009 | Ueda et al. | |
| 2009/0245553 A1 | 10/2009 | Parker | |
| 2009/0245554 A1 | 10/2009 | Parker | |
| 2009/0245555 A1 | 10/2009 | Parker et al. | |
| 2009/0247810 A1 | 10/2009 | Parker et al. | |
| 2009/0247811 A1 | 10/2009 | Parker | |
| 2009/0248085 A1 | 10/2009 | Parker | |
| 2009/0248086 A1 | 10/2009 | Parker | |
| 2009/0281367 A1 | 11/2009 | Cho | |
| 2010/0016985 A1 * | 1/2010 | Rabiei | A61K 6/08 623/23.6 |
| 2010/0179375 A1 | 7/2010 | Andersson | |
| 2010/0274099 A1 * | 10/2010 | Telfort | A61B 5/6843 600/300 |
| 2010/0298626 A1 | 11/2010 | Andersson et al. | |
| 2011/0275947 A1 * | 11/2011 | Feldman | A61N 1/0563 600/508 |
| 2012/0088957 A1 | 4/2012 | Adamson et al. | |
| 2012/0116228 A1 * | 5/2012 | Okubo | A61B 8/00 600/459 |
| 2012/0253104 A1 | 10/2012 | Andersson et al. | |
| 2013/0172662 A1 | 7/2013 | Menzl et al. | |

FOREIGN PATENT DOCUMENTS

| | | |
|---|---|---|
| JP | 64073781 A | 3/1989 |
| JP | 01-290272 A | 11/1989 |
| WO | 97/30565 A1 | 8/1997 |
| WO | 01/93633 A1 | 12/2001 |
| WO | 01/93634 A1 | 12/2001 |
| WO | 01/93635 A1 | 12/2001 |
| WO | 03/001846 A1 | 1/2003 |
| WO | 03/096744 A1 | 11/2003 |
| WO | 2004/032566 A1 | 4/2004 |
| WO | 2004/043290 A2 | 5/2004 |
| WO | 2007/024657 A2 | 3/2007 |
| WO | 2007/052251 A2 | 5/2007 |
| WO | 2008/143573 A1 | 11/2008 |
| WO | 2009/121104 A1 | 10/2009 |
| WO | 2009/121116 A9 | 11/2009 |

OTHER PUBLICATIONS

International Search Report and Written opinion for International Application No. PCT/IB2012/051574 dated Nov. 9, 2012.

Janocha, "Actuators: Basics and Applications", Springer Verlag 2004, Jul. 8, 2009, pp. 265-267, Available at: <http://books.qooqle.eom.au/books?id.

Juuti, et al., "Mechanically Amplified large displacement piezoelectric actuators", Sensors and Actuators A 120, Dec. 22, 2004, pp. 225-231.

International Search Report and Written opinion for International Application No. PCT/AU2009/000358 dated Jul. 14, 2009.

International Search Report and Written opinion for International Application No. PCT/AU2009/000372 dated Jun. 29, 2009.

Written Opinion for International Application No. PCT/SE2008/000336 dated Sep. 3, 2008.

Zhou, et al., "Analysis of a diamond-shaped mechanical amplifier for a piezo actuator", Int J Adv Manuf Technol, vol. 32, 2007, pp. 1-7.

Piezomechanik GmbH, "Piezoelectric bending actuators, Disk translators ("bimorphs"), Piezoelectric tubes," Mar. 2002, pp. 1-12.

Sichel, et al. "New Approach for Implantable Hearing Aids: A Feasibility Study" Ann Otol Rhinol Larynqol. 113:2004, pp. 936-940.

Selection guide for piezo actuators. Cedrat Technologies—Piezo Products Catalogue—Version 3.0—Sep. 2003.

* cited by examiner

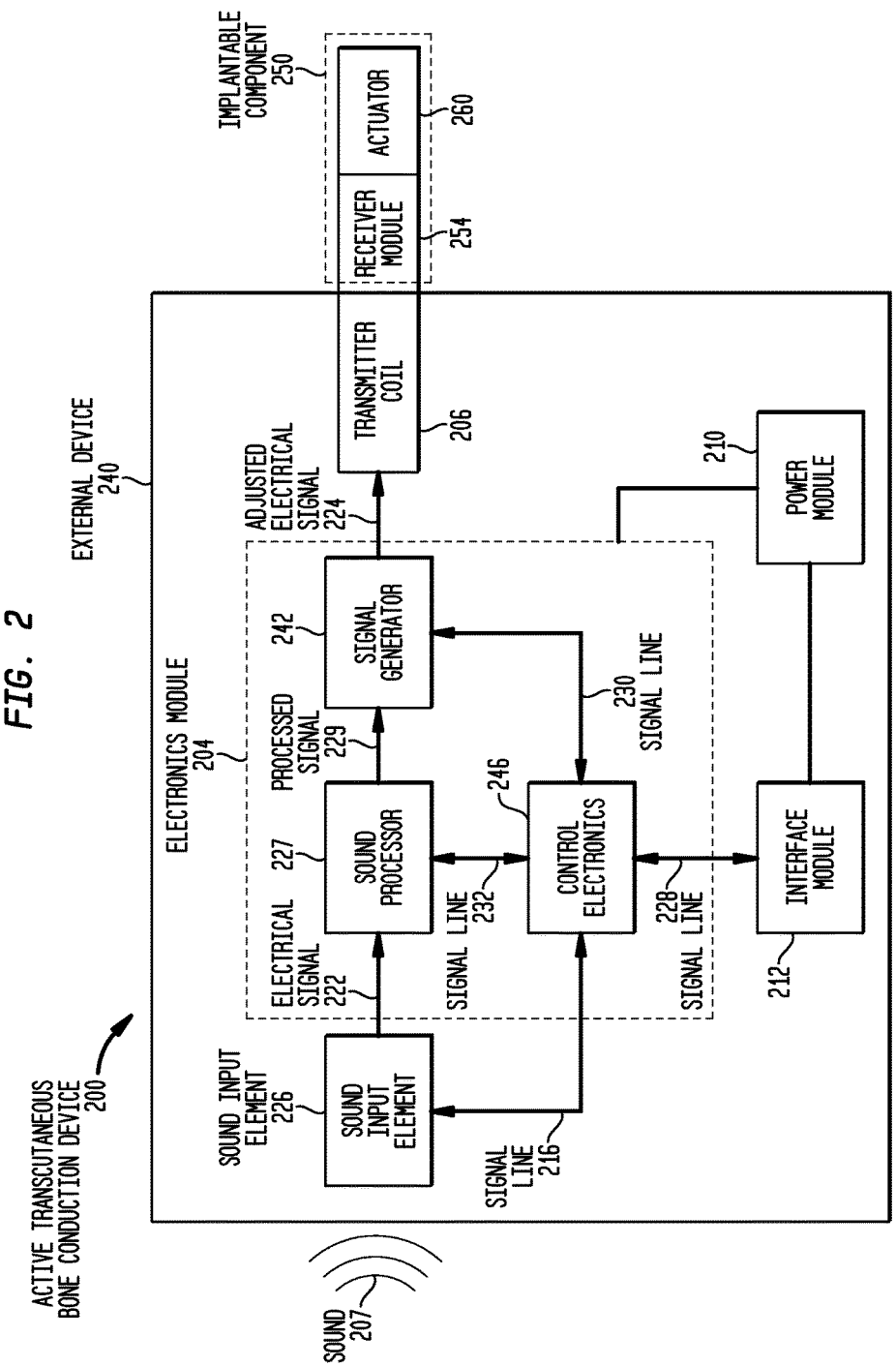

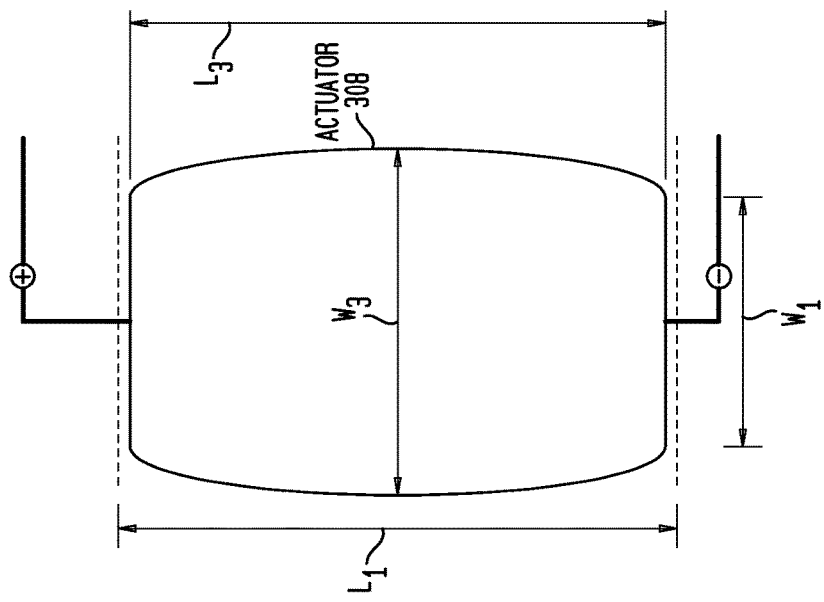
FIG. 3D
FIG. 3C
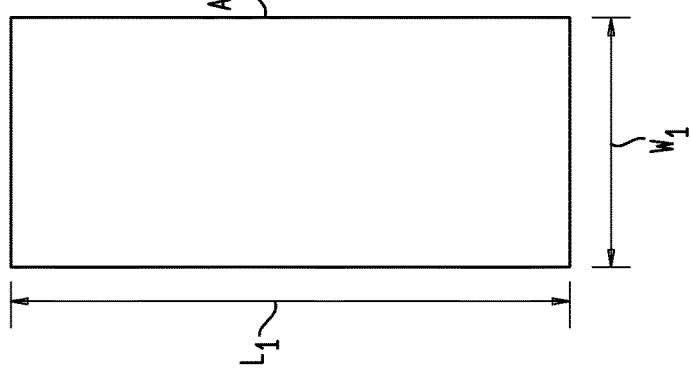
FIG. 3B

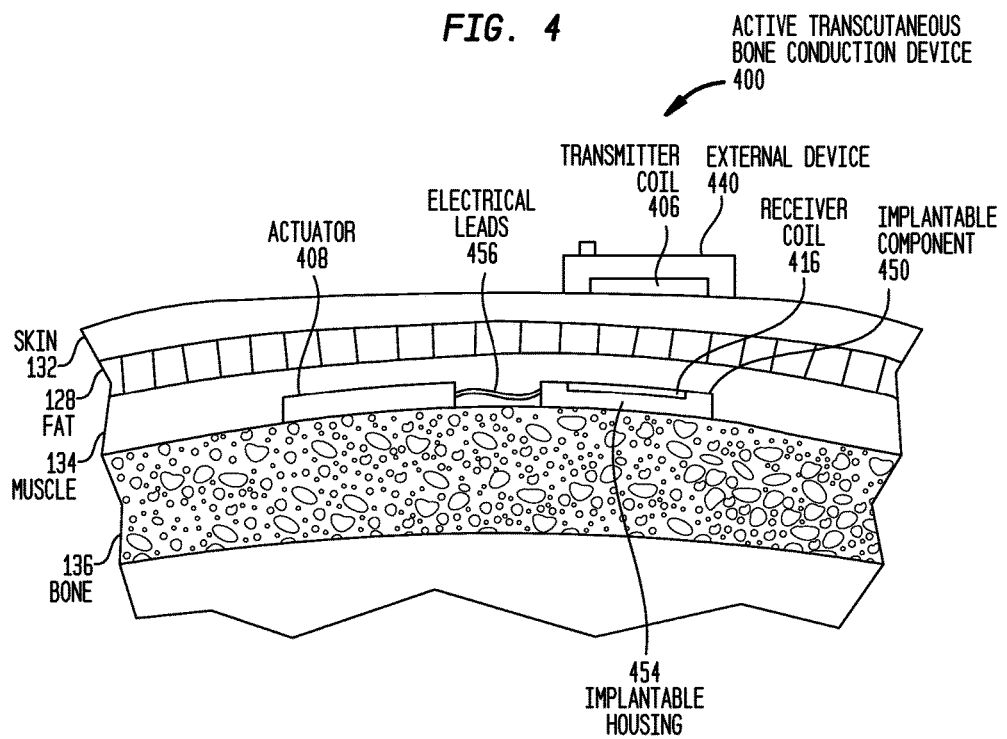

FIG. 8

| THICKNESS IN mm | OUTER DIAMETER IN mm | | | | | | | | | |
|---|---|---|---|---|---|---|---|---|---|---|
| | 3 | 5 | 10 | 15 | 20 | 25 | 35 | 40 | 45 | 50 |
| | | | | | | | | | | |
| 0.20 | ▨ | ▨ | ▨ | ▨ | ▨ | | | | | |
| 0.25 | ▨ | ▨ | ▨ | ▨ | ▨ | | | | | |
| 0.30 | ▨ | ▨ | ▨ | ▨ | ▨ | ▨ | | | | |
| 0.40 | ▨ | ▨ | ▨ | ▨ | ▨ | ▨ | ▨ | | | |
| 0.50 | ▨ | ▨ | ▨ | ▨ | ▨ | ▨ | ▨ | ▨ | ▨ | |
| 0.75 | ▨ | ▨ | ▨ | ▨ | ▨ | ▨ | ▨ | ▨ | ▨ | ▨ |
| 1.00 | ▨ | ▨ | ▨ | ▨ | ▨ | ▨ | ▨ | ▨ | ▨ | ▨ |
| 2.00 | ▨ | ▨ | ▨ | ▨ | ▨ | ▨ | ▨ | ▨ | ▨ | ▨ |
| 3.00 | ▨ | ▨ | ▨ | ▨ | ▨ | ▨ | ▨ | ▨ | ▨ | ▨ |
| 4.00 | ▨ | ▨ | ▨ | ▨ | ▨ | ▨ | ▨ | ▨ | ▨ | ▨ |
| 5.00 | ▨ | ▨ | ▨ | ▨ | ▨ | ▨ | ▨ | ▨ | ▨ | ▨ |
| 10.00 | ▨ | ▨ | ▨ | ▨ | ▨ | ▨ | ▨ | ▨ | ▨ | ▨ |
| 20.00 | ▨ | ▨ | ▨ | ▨ | ▨ | ▨ | ▨ | ▨ | ▨ | ▨ |

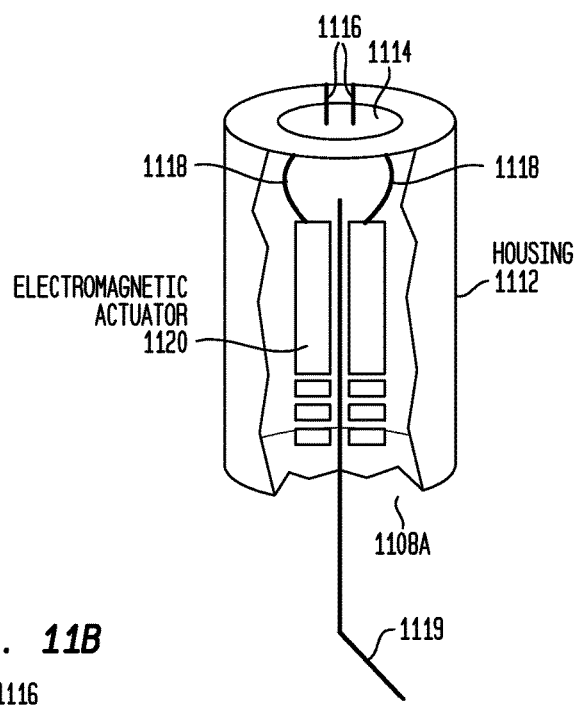
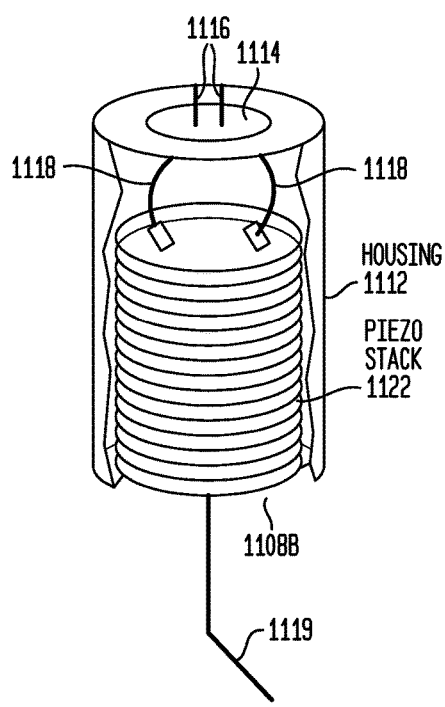
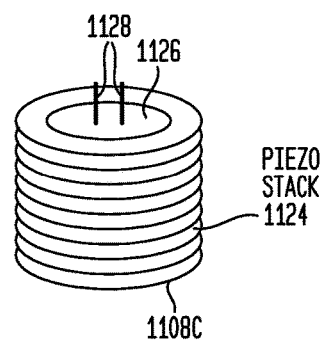

HEARING PROSTHESIS WITH A PIEZOELECTRIC ACTUATOR

This application is a continuation application of U.S. application Ser. No. 13/078,402 filed Apr. 1, 2011, naming Marcus Andersson as an inventor, the contents of this application being hereby incorporated by reference herein in its entirety.

BACKGROUND

Field of the Invention

The present invention relates generally to hearing prostheses, and more particularly, to a hearing prosthesis with a piezoelectric actuator.

Related Art

Hearing loss, which may be due to many different causes, is generally of two types: conductive and sensorineural. Sensorineural hearing loss is due to the absence or destruction of the hair cells in the cochlea that transduce sound signals into nerve impulses. Various hearing prostheses are commercially available to provide individuals suffering from sensorineural hearing loss with the ability to perceive sound. For example, cochlear implants use an electrode array implanted in the cochlea of a recipient to bypass the mechanisms of the ear. More specifically, an electrical stimulus is provided via the electrode array to the auditory nerve, thereby causing a hearing percept.

Conductive hearing loss occurs when the normal mechanical pathways that provide sound to hair cells in the cochlea are impeded, for example, by damage to the ossicular chain or ear canal. Individuals suffering from conductive hearing loss may retain some form of residual hearing because the hair cells in the cochlea may remain undamaged.

Individuals suffering from conductive hearing loss typically receive an acoustic hearing aid. Hearing aids rely on principles of air conduction to transmit acoustic signals to the cochlea. In particular, a hearing aid typically uses an arrangement positioned in the recipient's ear canal or on the outer ear to amplify a sound received by the outer ear of the recipient. This amplified sound reaches the cochlea causing motion of the perilymph and stimulation of the auditory nerve.

In contrast to hearing aids, certain types of hearing prostheses commonly referred to as bone conduction devices, convert a received sound into mechanical vibrations. The vibrations are transferred through the skull to the cochlea causing generation of nerve impulses, which result in the perception of the received sound. Bone conduction devices may be a suitable alternative for individuals who cannot derive sufficient benefit from acoustic hearing aids, cochlear implants, etc.

Other types of hearing prostheses commonly referred to as middle-ear implants, also convert received sound into vibrations. The vibrations are delivered to the middle ear or inner ear, and are thereafter transferred to the cochlea causing generation of nerve impulses, which result in the perception of the received sound.

SUMMARY

In accordance with one aspect of the present invention, there is a hearing prosthesis comprising, an actuator including a material that deforms in response to an electrical signal and that is adapted to, upon implantation in a recipient, transmit vibrations representative of a sound signal to an organ of the recipient, wherein the material is at least partially exposed to at least one of body tissue and fluid of the recipient.

In accordance with another aspect of the present invention, there is a hearing prosthesis comprising actuator means for deforming in accordance with an electrical sound signal to vibrate a hearing organ of a recipient, wherein the means is at least partially exposed to at least one of internal body tissue and fluid of the recipient.

In accordance with yet another aspect of the present invention, there is a transducer, comprising a material that generates electricity when deformed, wherein the material is adapted to be at least partially exposed to at least one of body tissue and fluid of the recipient.

In accordance with another aspect of the present invention, there is a method of imparting vibrational energy to bone, the method comprising deforming a deformable material in response to an electric signal applied thereto, and imparting vibrational energy resulting from the deformation of the deformable material directly from the deformable material to the bone.

BRIEF DESCRIPTION OF THE DRAWINGS

Embodiments of the present invention are described below with reference to the attached drawings, in which:

FIG. 2 is a functional block diagram of a bone conduction device in accordance with an embodiment of the present invention;

FIGS. 3B-3D are schematic diagrams illustrating an exemplary principle of operation of a piezoelectric material subjected to an electrical signal;

FIG. 4 is a schematic diagram presenting an exemplary embodiment of an active transcutaneous bone conduction device according to the present invention;

FIG. 8 presents a chart including exemplary dimensions of a component used in an exemplary embodiment of the present invention.

FIG. 11A is a perspective view of an exemplary actuator usable with hearing prostheses;

FIG. 11B is a perspective view of an exemplary actuator according to an embodiment of the present invention;

FIG. 11C is a perspective view of another exemplary actuator according to an embodiment of the present invention;

DETAILED DESCRIPTION

Aspects of the present invention are generally directed to a hearing prosthesis actuator having a piezoelectric material to be implanted in a recipient to be at least partially exposed to the recipient's body tissue and/or fluid. That is, there is no housing or other type of barrier forming a hermetic seal between the piezoelectric material and the organic environment in which it is implanted. In exemplary embodiments, the piezoelectric material is barium titanate (BaTiO$_3$) and/or strontium titanate (SrTiO$_3$).

Because the piezoelectric material is biocompatible, no housing is interposed between the actuator and the organic environment of the recipient, enabling the material to directly osseointegrate to tissue (e.g., bone) of the recipient. This reduces losses of vibrational energy as vibrations are transferred from the actuator to the tissue.

By "biocompatible," it is meant that the piezoelectric material is a material that would meet regulatory approval by at least one of the United States, Japan and the European Union for implantation into a human such that the material would be at least partially exposed for a long term to the recipient's body tissue and/or fluid.

Figure 1:
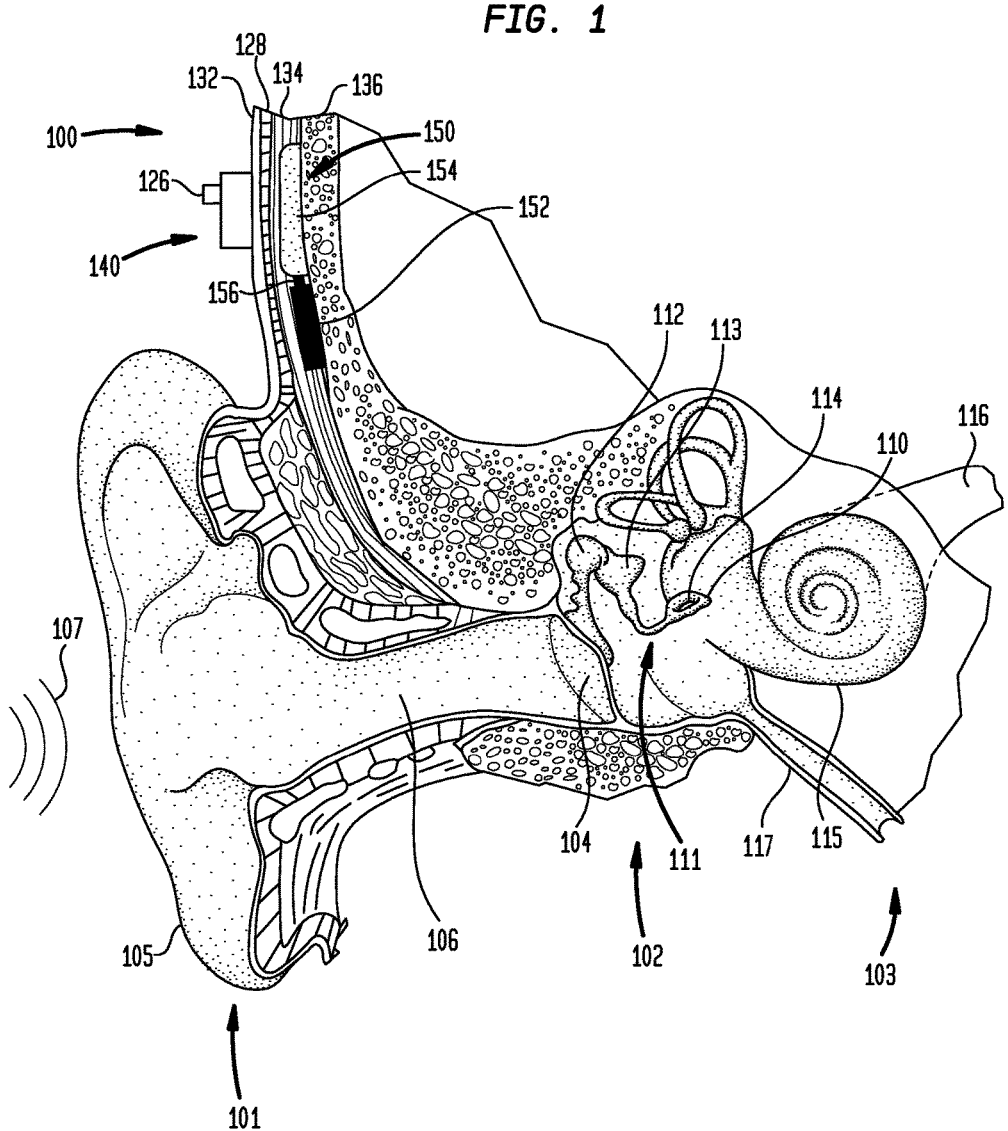
FIG. 1 is a perspective view of an exemplary bone conduction device in which embodiments of the present invention may be implemented.

FIG. 1 is a perspective view of an active transcutaneous bone conduction device 100 in which embodiments of the present invention may be implemented. As shown, the recipient has an outer ear 101, a middle ear 102 and an inner ear 103. Elements of outer ear 101, middle ear 102 and inner ear 103 are described below, followed by a description of bone conduction device 100.

In a fully functional human hearing anatomy, outer ear 101 comprises an auricle 105 and an ear canal 106. A sound wave or acoustic pressure 107 is collected by auricle 105 and channeled into and through ear canal 106. Disposed across the distal end of ear canal 106 is a tympanic membrane 104 which vibrates in response to acoustic wave 107. This vibration is coupled to oval window or fenestra ovalis 110 through three bones of middle ear 102, collectively referred to as the ossicles 111 and comprising the malleus 112, the incus 113 and the stapes 114. The ossicles 111 of middle ear 102 serve to filter and amplify acoustic wave 107, causing oval window 110 to vibrate. Such vibration sets up waves of fluid motion within cochlea 139. Such fluid motion, in turn, activates hair cells (not shown) that line the inside of cochlea 139. Activation of the hair cells causes appropriate nerve impulses to be transferred through the spiral ganglion cells and auditory nerve 116 to the brain (not shown), where they are perceived as sound.

FIG. 1 also illustrates the positioning of bone conduction device 100 relative to outer ear 101, middle ear 102 and inner ear 103 of a recipient of device 100. As shown, bone conduction device 100 is positioned behind outer ear 101 of the recipient. The bone conduction device 100 comprises an external component 140 and implantable component 150. The bone conduction device 100 includes a sound input element 126 to receive sound signals. Sound input element may comprise, for example, a microphone, telecoil, etc. In an exemplary embodiment, sound input element 126 may be located, for example, on or in bone conduction device 100, or on a cable extending from bone conduction device 100. The sound input element 126 may be part of the external component 140 as shown, or may be part of the implantable component 150 (e.g., it may be subcutaneously implanted in the recipient). Sound input element 126 may also be a component that receives an electronic signal indicative of sound, such as, for example, from an external audio device. For example, sound input element 126 may receive a sound signal in the form of an electrical signal from an MP3 player electronically connected to sound input element 126.

Bone conduction device 100 comprises a sound processor, a vibrating piezoelectric actuator and/or various other operational components. More particularly, sound input device 126 (e.g., a microphone) converts received sound signals into electrical signals. These electrical signals are processed by the sound processor. The sound processor generates control signals which cause the actuator to vibrate. In other words, the actuator converts the electrical signals into mechanical motion to impart vibrations to the recipient's skull.

As noted above, bone conduction device 100 is an active transcutaneous bone conduction device. That is, at least one active component (e.g. the piezoelectric actuator) 152 is implanted beneath the skin and is thus part of the implantable component 150. That is, implantable component 150 is configured to generate stimulation mechanical force that is conducted via one or more recipient's bones to produce an auditory stimulation. Additional details of such embodiments are described in greater detail below.

As described below, external component 140 may comprise a sound processor and signal transmitter, while implantable component 150 may comprise a signal receiver and/or various other electronic circuits/devices contained in implantable housing 154. As may be seen, implantable housing 154 is in electrical communication with active component 152 via electrical leads 156. These features and other features of the implantable component 150 are discussed in greater detail below.

In accordance with embodiments of the present invention, the active component 152 is in direct contact with bone 136. As will be discussed in greater detail below, the active component 152 may be a piezoelectric actuator that is osseointegrated to the bone 136.

A functional block diagram of one embodiment of active transcutaneous bone conduction device 100, referred to as active transcutaneous bone conduction device 200, is shown in FIG. 2. In the illustrated embodiment, a sound 207 is received by a sound input element 226 of external device 240, the sound input element 226 corresponding to sound input element 126 detailed above. In some embodiments, sound input element 226 is a microphone configured to receive sound 207, and to convert sound 207 into an electrical signal 222. As described below, in other embodiments sound 207 may be received by sound input element 226 already in the form of an electrical signal 222 and thus, in some embodiments, it is not converted by sound input element 226.

As shown in FIG. 2, electrical signal 222 is output by sound input element 226 to an electronics module 204. Electronics module 204 is configured to convert electrical signal 222 into an adjusted electrical signal 224. As described below in more detail, electronics module 204 may include a sound processor, control electronics, and a variety of other elements. FIG. 2 also illustrates a power module 210. Power module 210 provides electrical power to one or more components of active transcutaneous bone conduction device 200. For ease of illustration, power module 210 has been shown connected only to interface module 212 and electronics module 204. However, it should be appreciated that power module 210 may be used to supply power to any electrically powered circuits/components of active transcutaneous bone conduction device 200.

Active transcutaneous bone conduction device 200 further includes an interface module 212 that allows the recipient to interact with device 200. For example, interface module 212 may allow the recipient to adjust the volume, alter the speech processing strategies, power on/off the device, etc. Interface module 212 communicates with electronics module 204 via signal line 228.

In the embodiment illustrated in FIG. 2, sound input element 226, electronics module 204, power module 210 and interface module 212 may be integrated in a single housing, all of these components collectively corresponding to external device 140 detailed above. However, it should be appreciated that in certain embodiments of the present invention, one or more of the illustrated components may be housed in separate or different housings. Similarly, it should also be appreciated that in such embodiments, direct connections between the various modules and devices are not necessary and that the components may communicate, for example, via wireless connections.

As may be seen from FIG. 2, electronics module 204 comprises a sound processor 227, signal generator 242 and control electronics 246, signal generator 242 being in electrical communication with control electronics 246 via signal line 230. Sound input element 226 is also in electrical communication with control electronics 246 via signal line 216. As explained above, in certain embodiments sound input element 226 comprises a microphone configured to convert a received acoustic signal into electrical signal 222. FIG. 2 also shows that sound processor 227 is in electrical communication with control electronics 246 via signal line 232.

In embodiments of the present invention, electrical signal 222 is output from sound input element 226 to sound processor 227. Sound processor 227 uses one or more of a plurality of techniques to selectively process, amplify and/or filter electrical signal 222 to generate a processed signal 229. In certain embodiments, sound processor 227 may comprise substantially the same sound processor as is used in an air conduction hearing aid. In further embodiments, sound processor 227 comprises a digital signal processor.

Processed signal 229 is provided to signal generator 242. Signal generator 242 outputs the adjusted electrical signal 224 to a transmitter module which comprises a transmission device such as, for example, a transmitter coil 206 that, in some embodiments, establishes an inductive transcutaneous link with a receiver coil in the implantable component 150. More specifically, adjusted electrical signal 224 is transmitted via transmitter coil 206 of the transmitter module to a receiver coil (not shown) of receiver module 254 of the implantable component 250, which, in some embodiments, corresponds to implantable component 150 detailed above with respect to FIG. 1. In some embodiments, receiver module 254 corresponds to or is in electrical communication with implantable housing 154 detailed above with respect to FIG. 1. Actuator 260, which is in electrical communication with receiver module 254 generates mechanical vibration that is communicated through the recipient's bone in order to provide stimulation to the auditory nerve of the recipient.

For ease of description the signal supplied by signal generator 242 via the transmitter module to actuator 260 has been referred to as an adjusted electrical signal 224. In some embodiments, it may be an actuator control signal. In some embodiments, the adjusted electrical signal 224 may comprise an unmodified version of processed signal 229, which may be further processed in implantable component 250 in other embodiments of the present invention.

In one embodiment of the present invention, actuator 260 generates an output force that causes movement of the cochlea fluid so that a sound may be perceived by the recipient. The output force may result in mechanical vibration of the recipient's skull, or in physical movement of the skull about the neck of the recipient. As noted above, in certain embodiments, active transcutaneous bone conduction device 200 delivers the output force to the skull of the recipient via direct contact of actuator 260 with the recipient's bone. Actuator 260 may be made of a biocompatible piezoelectric material as detailed herein.

Figure 3A:
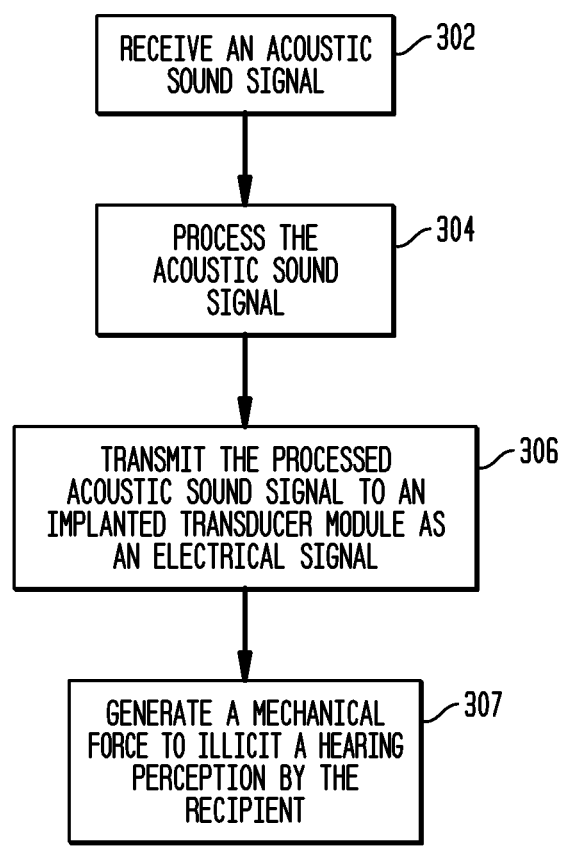
FIG. 3A is a flowchart illustrating the conversion of an input sound to skull vibration in a bone conduction device according to an embodiment of the present invention.

FIG. 3A illustrates the conversion of an input sound signal into a mechanical force for delivery to the recipient's skull in accordance with embodiments of active transcutaneous bone conduction device 200. At block 302, a sound signal 207 is received by the device of the present invention. In certain embodiments, the sound signal is received via microphones. In other embodiments, the input sound signal is received via an electrical input. In still other embodiments, a telecoil integrated in, or connected to, active transcutaneous bone conduction device 200 may be used to receive the sound signal.

At block 304, the sound signal received by active transcutaneous bone conduction device 200 is processed by the speech processor in electronics module 204. As explained above, the speech processor may be similar to speech processors used in acoustic hearing aids. In such embodiments, speech processor may selectively amplify, filter and/or modify the sound signal. For example, the speech processor may be used to eliminate background or other unwanted noise signals received by active transcutaneous bone conduction device 200.

At block 306, the processed sound signal is provided to implantable component 250 as an electrical signal. At block 307, implantable component 250 converts the electrical signal into a mechanical force configured to be delivered to the recipient's skull so as to illicit a hearing perception of the sound signal.

As noted above, embodiments of the present invention utilize a material, such as a piezoelectric material, that deforms (e.g., expands and/or contracts) when exposed to an electrical signal. Piezoelectric elements that may be used in embodiments of the present invention may comprise, for example, piezoelectric crystals, piezoelectric ceramics, or some other material exhibiting a deformation in response to an applied electrical signal. FIGS. 3B-3D schematically depicts this phenomenon. Initially, as depicted in FIG. 3B, the actuator 308 made of piezoelectric material is not subjected to any electrical signal. The actuator 308 thus has a length $L_1$ and a thickness $W_1$, as may be seen in FIG. 3B. Then, an electrical signal is applied to the actuator 308 having a first polarity, as depicted with respect to actuator 308 in FIG. 3C. This causes a deformation in the actuator 308 in response to the application of the electric signal. Specifically, as may be seen, the length of the actuator 308 expands from $L_1$ and the width of the actuator contracts from $W_1$ at least away from the ends. Next, the electrical signal applied to the actuator 308 has a polarity opposite to that applied with respect to FIG. 3C. This is depicted with respect to actuator 308 in FIG. 3D. As may be seen, the length of the actuator 308 in FIG. 3D has contracted from $L_1$ and the width of the actuator 308 in FIG. 3D has expanded from $W_1$.

It is noted that in some embodiments, there is no polarity reversal of the electrical signal. That is, the electrical signal is applied in a binary manner. If the electrical signal applied has a polarity as depicted with respect FIG. 3C, the actuator 308 will expand from its length $L_1$ and/or contract from its width $W_1$ without charge (i.e., the actuator 308 depicted in FIG. 3B). If the electrical signal applied has a polarity as depicted with respect to FIG. 3D, the actuator 308 will contract from its length $L_1$ and/or expand from its width $W_1$ without charge. Removal of the electrical signal returns the actuator 308 to its length $L_1$ and/or its width $W_1$ without charge. It is further noted that in some embodiments, combinations of the application of an electrical signal applied in a binary manner and the application of the electrical signal with reversing polarity may be utilized.

It is noted in some embodiments, upon the application of an electrical signal, the length of the actuator 308 may stay the same and only the width changes or the width may stay the same and only the length changes. Also, in some embodiments, the width and the length both increase and decrease with the application of a charge with a given polarity.

FIG. 4 illustrates one embodiment of the present invention in which an active transcutaneous bone conduction device 400 includes an external device 440 and an implantable component 450 that is implanted beneath the various tissue layers shown. In some embodiments of the present invention, the external device 440 corresponds to the external devices 140 and 240 detailed above, and the implantable component 450 corresponds to the implantable components 150 and 250 detailed above. As may be seen, the implantable component 450 includes actuator 408 that is in direct contact with the outer surface of the recipient's skull. That is, the actuator 408 is in substantial contact with the recipient's bone 136 such that vibration forces from the actuator 408 are communicated from actuator 408 to the recipient's bone 136. It is noted that in some embodiments, there may be one or more thin non-bone tissue layers between actuator 408 and the recipient's bone (bone tissue) while still permitting sufficient support so as to allow efficient communication of the vibration forces generated by actuator 408 to recipient's bone 136.

In the embodiment illustrated in FIG. 4, transmitter coil 406 of external device 440 transmits inductance signals to receiver coil 416 in an implantable housing 454 of implantable component 450. Implantable housing 454 may correspond to receiver module 254 detailed above. An electronics assembly (not shown) contained in implantable housing 454 then generates electrical signals (by outputting the signals received by receiver coil 416 and/or processing/amplifying the signals received by receiver coil 416) which are conducted via electrical leads 456 to actuator 408, whereupon actuator 408 vibrates upon receipt of those signals. It is noted that in other embodiments of the present invention, the actuator 408 may be positioned with such proximity to the implantable housing 454 that electrical leads 456 are not present, as will be described in greater detail below.

In an exemplary embodiment of the present invention, the actuator 408 is made of/includes a material that expands and/or contracts in response to an electrical signal delivered via electrical leads 456 to the actuator 408. In this exemplary embodiment, this material is exposed to tissue (including bone 136, muscle 134 and/or fat 128, which are covered by skin 132) and/or body fluids of the recipient, as may be seen in FIG. 4. Further, in this exemplary embodiment, the material is a piezoelectric material.

By 'exposed to tissue and/or body fluids,' it is meant that a hermetic barrier is not present between the piezoelectric material and the tissue and/or body fluids that would substantially inhibit leaching of elements and/or compounds of the piezoelectric material into the tissue and/or body fluids. In this regard, embodiments where the material that deform in response to an electrical signal is in direct contact with the skull (e.g., no barrier is interposed between the material and the skull) permits the impartation of vibrational energy resulting from the deformation of the deformable material directly from the deformable material to the skull. By 'directly from the deformable material to the skull,' it is meant that the vibrations do not pass through an intermediate component, such as a hermetic layer or hermetic housing to reach the skull.

In an exemplary embodiment, the piezoelectric material forming actuator 408 is a titanate, such as, for example, barium titanate ($BaTiO_3$, hereinafter "BTO") and/or strontium titanate ($SrTiO_3$, hereinafter, STO). It is noted that non-biocompatible piezoelectric materials such as lead zirconate titanate (hereinafter PZT), which contains lead, should only be implanted in a human when hermetically shielded from human tissue and/or body fluids. Accordingly, an embodiment of the present invention includes an actuator 408 made from piezoelectric material substantially devoid of non-biocompatible substances in general and lead and/or PZT in particular. In some embodiments utilizing biocompatible materials to form actuator 408, improved acoustic coupling of the actuator 408 to the bone and, therefore, improved efficiency and performance is achieved because the piezoelectric material of the actuator need not be separated from the tissue and/or body fluids of the recipient by a hermetic barrier. This may provide higher efficiency vis-à-vis performance of the active transcutaneous bone conduction device in which such an actuator is used, not to mention enabling relatively simpler, smaller and/or less expensive actuator designs. The coupling between the bone of the recipient and the actuator may result in less loss of energy than if the actuator were placed in a housing.

In yet other exemplary embodiments, the piezoelectric material forming actuator 408 may be lithium niobate (LiNbO$_3$) and/or lithium tantalate (LiTaO$_3$). In some embodiments, these materials may enhance osseointegration of the actuator to the skull.

In an exemplary embodiment of the present invention, such as in an embodiment where the piezoelectric material substantially comprises BTO, the piezo coefficient of the piezoelectric material used in the actuator 408 is 460 pC/N and/or has an acoustic impedance of 20 Mrayl (20·10$^6$ N·s·m$^{-3}$). Accordingly, some embodiments utilize a piezoelectric material having an acoustic impedance that more closely matches that of human bone. In some such embodiments, this reduces the mismatch between the acoustical impedance of the actuator and the skull bone, thereby reducing energy losses at the boundary between the piezoelectric material and the bone.

More specific exemplary features of exemplary actuators that may be used as actuator 408 will now be described.

As noted above, in an exemplary embodiment of the present invention, a portion of the actuator 408 is exposed to tissue and/or body fluids of the recipient. In one embodiment of the present invention as may be seen in FIG. 5A, there is an actuator 508A corresponding to an embodiment of actuator 408 that is substantially entirely made from/substantially entirely comprises biocompatible materials in general and piezoelectric materials in particular. In one such exemplary embodiment, the piezoelectric material(s) is BTO and/or STO. By way of example, such an actuator 508A may be in the form of a plate made of a piezoelectric material such as BTO and/or STO. The actuator 508A may be in the form of a ceramic. It may be cut from a single crystal of BTO and/or STO. Various crystal structures may be utilized in some embodiments. In some embodiments, the piezoelectric material forming actuator 508A may be doped with other biocompatible components, such as those that may further enhance osseointegration, as will be detailed below. As may be seen by way of example, the actuator is substantially a monolithic component.

Figure 5A:
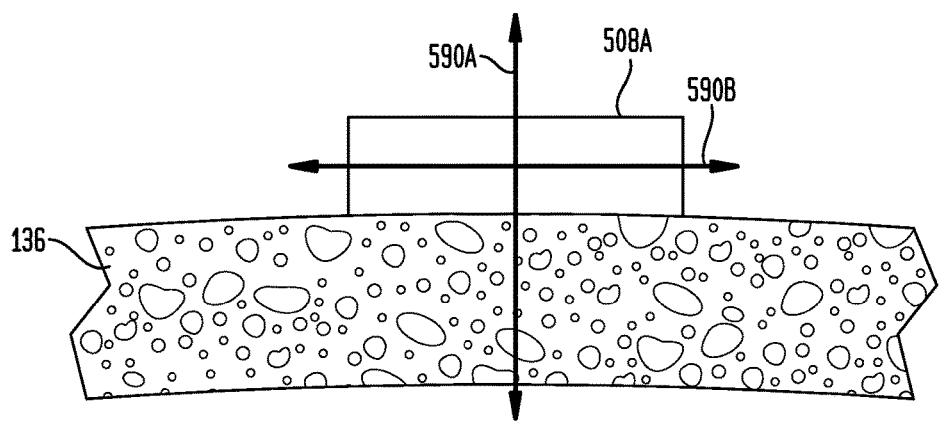
FIG. 5A is a schematic diagram presenting an exemplary embodiment of an actuator used in an active transcutaneous bone conduction device according to the present invention.
Figure 5B:
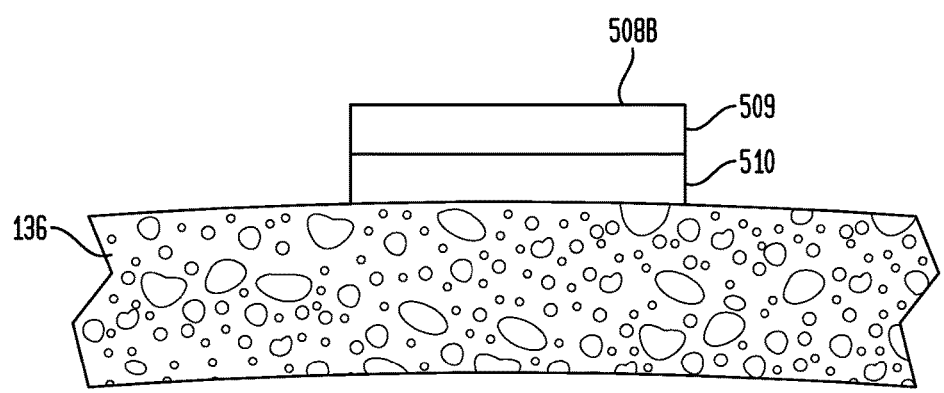
FIG. 5B is a schematic diagram presenting an alternative exemplary embodiment of an actuator used in an active transcutaneous bone conduction device according to the present invention.

In another embodiment of the present invention as may be seen in FIG. 5B, there is an actuator 508B corresponding to an embodiment of actuator 408 that, as with actuator 508A, is substantially entirely made from/substantially entirely comprises biocompatible materials. However, the actuator 508B is a composite actuator comprising two layers 509 and 510 (or more layers which are not shown). In one such exemplary embodiment, one or more of the layers 509 and 510 are piezoelectric materials such as BTO and/or STO. In other embodiments of the present invention, one of the layers 509 and 510 is made of a piezoelectric material, and the other layer is made of a non-piezoelectric material such as titanium. With respect to the embodiment depicted in FIG. 5B, the layer 510 is a piezoelectric material and layer 509 is titanium. As may be seen, the piezoelectric material of layer 510 is exposed to tissue of the recipient (bone 136, etc.). In an alternate embodiment, the layer 509 is a piezoelectric material and layer 510 is titanium, the piezoelectric material of layer 509 still being exposed to tissue of the recipient.

Figure 5C:
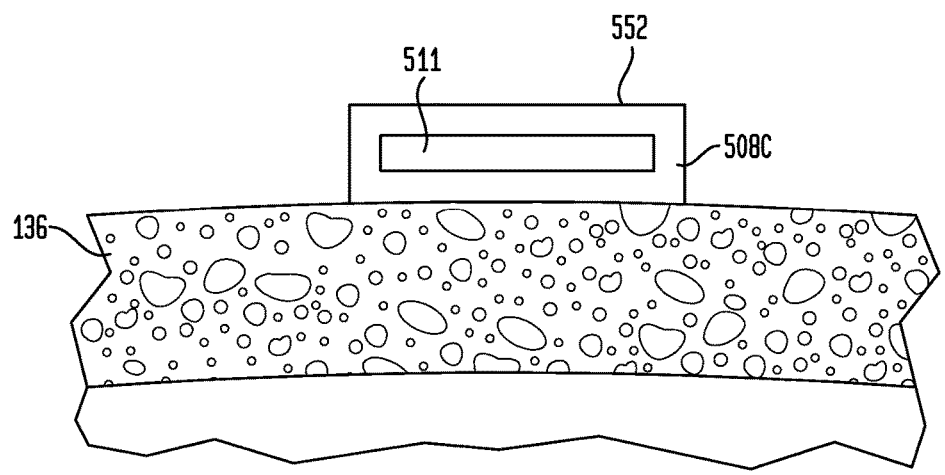
FIG. 5C is a schematic diagram presenting another alternative exemplary embodiment of an actuator used in an active transcutaneous bone conduction device according to the present invention.

In another embodiment of the present invention as may be seen in FIG. 5C, there is an active component 552 comprising an actuator 508C that, as with actuator 508A, is substantially entirely made from/substantially entirely comprises biocompatible materials in general and piezoelectric materials in particular. However, the piezoelectric material(s) encase counterweight 511 (or may partially encase counterweight 511). In an exemplary embodiment, counterweight 511 may be a solid homogeneous mass of biocompatible material and/or may be a housing of biocompatible material housing a mass of non-biocompatible material (the housing forming a hermetic seal between the tissue and/or body fluids of the recipient and the non-biocompatible material). As may be seen, the piezoelectric material of actuator 508C is exposed to tissue of the recipient (bone 136, etc.) It is noted that in some embodiments, element 551 may instead be an implantable housing corresponding to implantable housing 454 detailed above.

Figure 5D:
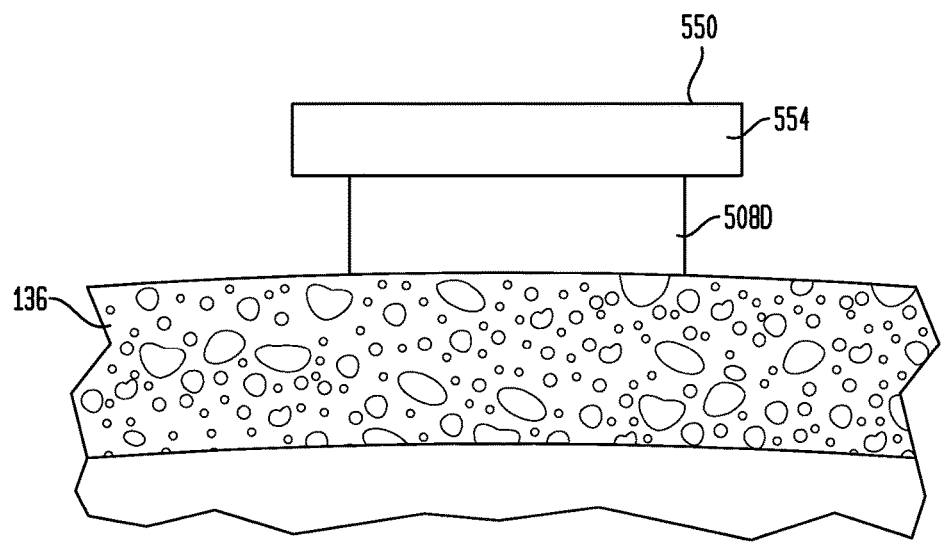
FIG. 5D is a schematic diagram presenting another alternative exemplary embodiment of an actuator used in an active transcutaneous bone conduction device according to the present invention.

In another embodiment of the present invention as may be seen in FIG. 5D, there is an implantable component 550 comprising an implantable housing 554, which may correspond to implantable housing 154 and/or 454 detailed above, and an actuator 508D that, as with actuator 508A, is substantially entirely made from/substantially entirely comprises biocompatible materials in general and piezoelectric materials in particular. However, as may be seen, implantable housing 554 is interposed on actuator 508D. In such embodiments, electrodes or the like may extend from implantable housing 554 to provide electrical signals to the piezoelectric materials of actuator 508D. As may be seen, the piezoelectric material of actuator 508D is exposed to tissue of the recipient (bone 136, etc.)

As referenced above, embodiments of the present invention include an actuator, such as actuator 508A of FIG. 5A, that includes piezoelectric material that is osseointegrated into the recipients skull. In an exemplary embodiment, the piezoelectric material is doped with or otherwise includes biocompatible components that form a biochemical bond to human bone, which in some embodiments is an osseointegrative bond. In some such embodiments, the doping component is hydroxyapatite and/or strontium and/or calcium. In an exemplary embodiment, calcium phosphate is used as a doping component. Any suitable material that enhances osseointegration of the piezoelectric material to the skull may be used in some embodiments of the present invention.

Some embodiments of the present invention include an actuator having a first surface formed by the piezoelectric material that is artificially roughened to have a first surface roughness. This first surface is adapted to abut and directly contact the recipient's skull. For example, referring to FIG. 5A, the first surface may be the surface of actuator 508A that contacts skull 136. The actuator 508A may have a second surface also formed by the material, but located away from the first surface, such as, with reference to FIG. 5A, surfaces on the left and/or right sides of actuator 508A, and/or the surface on the side of actuator 508A opposite the bottom surface. The second surface may have a second surface roughness. The first surface roughness of the first surface is significantly more rough than the second surface roughness of the second surface. By significantly more rough, it is meant that the roughness of the surface is such that the first surface roughness accelerates the osseointegration of the actuator to the skull at the first surface at a rate that is appreciably faster than what would be the case if the first surface had a surface roughness corresponding to the second surface roughness. In an exemplary embodiment, the first surface roughness is greater than that which would result from the normal manufacturing process of the actuator (e.g., that which would result from molding the actuator into its final form), the surface roughness resulting from the normal manufacturing process being the second surface roughness.

Figure 5E:
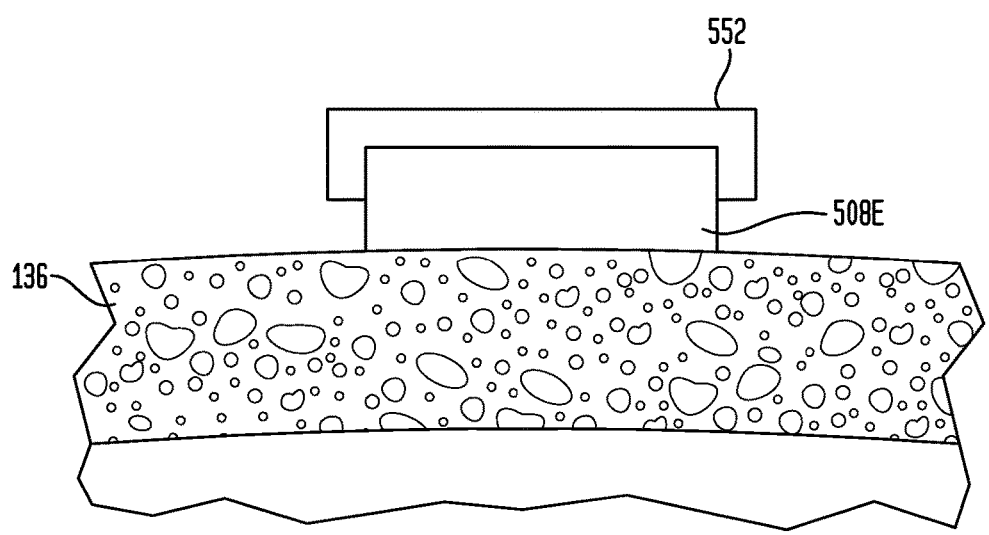
FIG. 5E is a schematic diagram presenting another alternative exemplary embodiment of an actuator used in an active transcutaneous bone conduction device according to the present invention.

Some embodiments of the present invention provide an active transcutaneous bone conduction device in which the implantable component is absent certain features that are present in other types of active transcutaneous bone conduction devices. For example, in at least some embodiments of the present invention utilizing the biocompatible piezoelectric material, there is no housing or other type of barrier (e.g., coating) that that provides a hermetic barrier between the piezoelectric material and the tissue and/or body fluids of the recipient. It is noted that some such embodiments may correspond to those of FIG. 5D or FIG. 5E, where a portion of the piezoelectric material is covered by or partially contained in, respectively, a non-piezoelectric component. In this regard, FIG. 5E depicts an active component 552 including a biocompatible, osseointegrating actuator 508E that is made entirely of BTO doped with osseointegrative enhancing components. A housing 552 covers the top and, partially, the sides of the actuator 508E. In an exemplary embodiment, the housing 552 is sufficiently flexible to at least effectively not impede movement of the actuator 508E. As may be seen, the housing 552 permits the actuator 508E to directly contact the skull 136.

Also, embodiments of the present invention may be practiced without a separate bone fixture (e.g., a component that includes a screw screwed into the skull and mechanically linked to the actuator) or the like to anchor the actuator to the recipient's skull. Instead, by osseointegrating the actuator to the skull, such a bone fixture is not needed. However, it is noted that in some embodiments, a bone fixture may be used with the actuator.

Figure 6A:
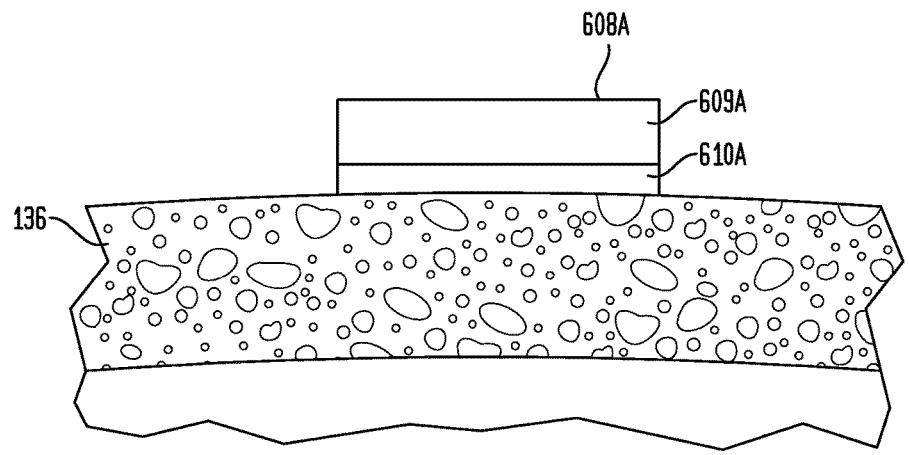
FIG. 6A is a schematic diagram presenting another alternative exemplary embodiment of an actuator used in an active transcutaneous bone conduction device according to the present invention.

FIG. 6A depicts an exemplary embodiment where a coating of biocompatible and/or bioactive material has been included in the actuator. Specifically, FIG. 6A depicts an actuator 608A made from a piezoelectric material 609A to which a biocompatible coating 610A has been applied. In the embodiment of FIG. 6A, the biocompatible coating 610A is a coating of a material that enhances osseointegration of the actuator 608A to the skull. It is noted that in some embodiments consistent with FIG. 6A, the piezoelectric material 609A is doped with a component that enhances osseointegration, as detailed above, while in others, it is not.

Figure 6B:
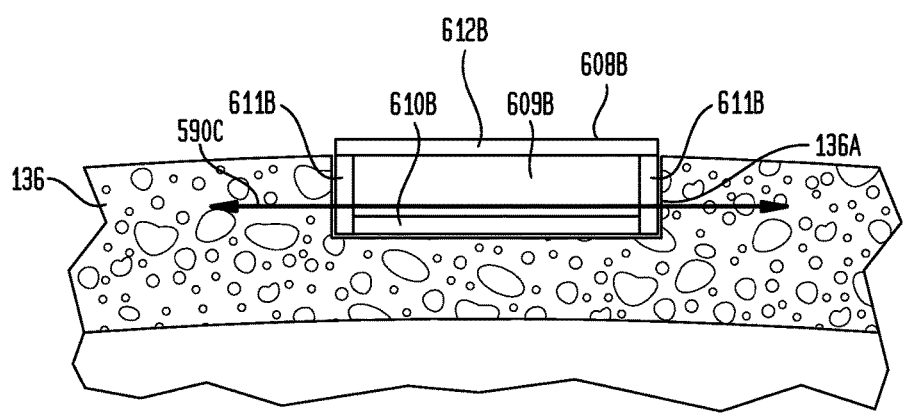
FIG. 6B is a schematic diagram presenting another alternative exemplary embodiment of an actuator used in an active transcutaneous bone conduction device according to the present invention.

It is noted that in other embodiments, the coatings of biocompatible and/or bioactive material may not enhance osseointegration. For example, the material may be an antibacterial material and/or a material that inhibits osseointegration. For example, FIG. 6B depicts another exemplary embodiment of the present invention, where a coating of biocompatible and/or bioactive material has been included in the actuator. Here, the actuator 608B is embedded, at least partially, in a recess 136A surgically cut into the skull 136. Biocompatible coatings 610B and 611B have been applied to the piezoelectric material 609B as may be seen. In the embodiment of FIG. 6B, the biocompatible coating 610B is a coating of a material that inhibits osseointegration of the bottom of the actuator 608B to the skull (e.g., silicon), and the biocompatible coatings 611B are coatings formed from a material that enhances osseointegration of the sides of the actuator 608B to the skull (e.g. hydroxyapatite). Thus, the actuator 608B expands and contracts with only the tensile and compressive reactive forces created by the sides of the recess in the skull resisting expansion and contraction of the actuator. That is, there is reduced (e.g., little to no) reactive shearing forces that might otherwise be present if the bottom of the actuator 608B was also osseointegrated to the skull.

In an exemplary embodiment, the actuators detailed herein may have a coating of titanium. The coating may be sputter coated onto the piezoelectric material.

Also, the embodiment of FIG. 6B includes an antibacterial coating 612B on top of the piezoelectric actuator. It is noted that in this embodiment, the piezoelectric material 609B is still exposed to tissue and/or body fluid of the recipient because at least one of the coatings is such that the piezoelectric material 609B is not hermetically sealed from the tissue and/or body fluid of the recipient.

Figure 6C:
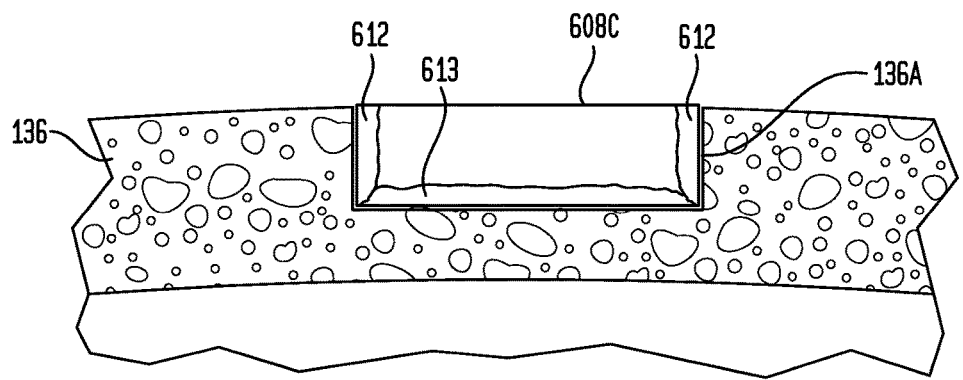
FIG. 6C is a schematic diagram presenting another alternative exemplary embodiment of an actuator used in an active transcutaneous bone conduction device according to the present invention.

FIG. 6C depicts another exemplary embodiment of the present invention, where the actuator 608C substantially comprises piezoelectric material. However, sections 612 of the actuator 608C have been doped with components that enhance osseointegration of the piezoelectric material to the skull, and section 613 of the actuator has been doped with a material that inhibits osseointegration of the piezoelectric material to the skull. The doping of this embodiment achieves at least similar functionality as the respective coatings detailed above with respect to FIG. 6B. Also, the embodiment of FIG. 6C may be doped with an antibacterial component.

Figure 6D:
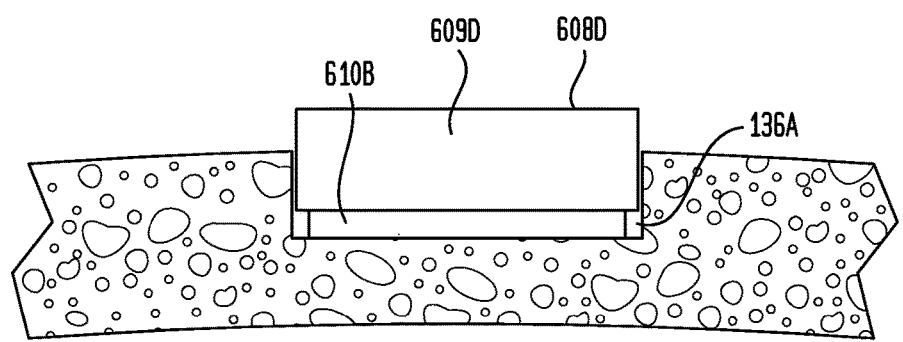
FIG. 6D is a schematic diagram presenting another alternative exemplary embodiment of an actuator used in an active transcutaneous bone conduction device according to the present invention.
Figure 6E:
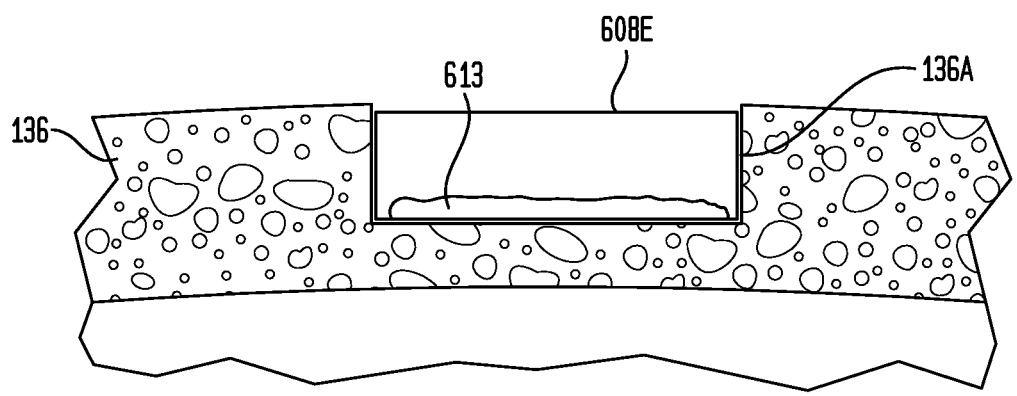
FIG. 6E is a schematic diagram presenting another alternative exemplary embodiment of an actuator used in an active transcutaneous bone conduction device according to the present invention.

It is noted that in embodiments where sufficient osseointegration of the piezoelectric material can be obtained without coatings/doping, embodiments may include only adding coatings that inhibit osseointegration/doping with components that inhibit osseointegration. In this regard, FIG. 6D depicts an exemplary actuator 608D that includes a layer 610B of osseointegrating material on the piezoelectric material 609D, and FIG. 6E depicts an exemplary actuator 608E with a section 613 doped with an osseointegration inhibiting component. The coating and doping of these embodiments achieve at least similar functionalities as the respective coating and doping detailed above with respect to FIG. 6B.

It is noted that in other embodiments, the various coatings and/or doped sections may be located at other locations in the actuator than those just detailed providing that such placement permits embodiments of the present invention to be practiced.

Embodiments of the present invention include a method of implanting an actuator in a recipient. In an exemplary embodiment, the actuator corresponds to any of the actuators disclosed herein, such as, for example, actuator 408 of FIG. 4. Initially, access to an interior of the recipient is surgically obtained. This may entail cutting through the recipient's skin to access the recipient's skull. Next, the interior of the recipient is surgically prepared for implantation of the actuator. This may entail removing a certain amount of bone tissue from the recipient to provide a recess, such as recess 136A described above with respect to FIG. 6B, for the actuator. In a subsequent step, the actuator is implanted within the recipient, such that the material that deforms in response to an electrical signal delivered thereto is exposed to tissue and/or body fluid of the recipient. In an exemplary embodiment, the actuator is placed such that the material is in direct contact with the skull of the recipient, such as, for example, is depicted in FIG. 6C. In an alternate embodiment of this method, the action of implanting the actuator within the recipient includes positioning the actuator in the recipient's middle ear or in the recipient's cochlea such that the first material is in direct contact with one or more structures of the recipient's ossiclular chain and/or the recipient's cochlea. Further embodiments of a system resulting from such a method and variations thereof are discussed in greater detail below.

Some additional features of some embodiments of the present invention will now be described.

Referring back to FIG. 5A, there is an implanted actuator 508A that is placed directly onto bone 136 without preparing a recess in the bone for the actuator 508A, where the implanted actuator 508A has osseointegrated to the bone 136, at least with respect to the bottom surface of the actuator 508A. During use, when an electrical signal is applied to actuator 508A, actuator 508A expands and/or contracts to impart a force in the vertical direction represented by arrow 590A. Vibrational energy generated via the expansion and/or contraction is imparted into the bone 136 due to the biochemical bond between the actuator 508A and the bone 136. In an alternative embodiment, still referring back to FIG. 5A, during use, when an electrical signal is applied to actuator 508A, actuator expands and/or contracts to impart a force in the horizontal direction represented by arrow 590B. Vibrational energy generated via the expansion and/or contraction is imparted into the bone 136 due to the biochemical bond between the actuator 508A and the bone 136.

It is noted that in some embodiments, actuators 508A may also expand and/or contract to impart force in the directions of both arrows 590A and 590B.

Referring now to FIG. 6B, where the actuator has been placed into a recess 136A in bone 136, and the actuator has osseointegrated to the bone 136 at desired locations, which may be established as detailed above, when an electrical signal is applied to actuator, the actuator expands and/or contracts to impart force in the horizontal direction represented by arrow 590C. Vibrational energy generated via the expansion and/or contraction is imparted into the bone 136 due to the biochemical bond between the actuator and the bone 136. It is noted that in some embodiments, the actuator may also expand and/or contract to impart forces in directions normal to arrow 590C in addition to or instead of directions parallel to arrow 590C.

In another embodiment of the present invention, there is an implanted actuator at least partially implanted in a recess of the skull (e.g., an actuator as depicted in FIG. 6B) that is a composite component that includes a counterweight/countermass and/or a non-osseointegrating component. The non-osseointegrating component is made of a material that inhibits osseointegration of that component to bone. A strata of piezoelectric material such as BTO and/or STO is attached to the non-osseointegrated component, this strata sandwiching the non-osseointegrating component with the counterweight/countermass. As just noted, this actuator may be placed at least partially into a recess in bone, such that at least the strata of piezoelectric material and at least a portion of the non-osseointegrating component are located in the recess. Over time, the actuator osseointegrates to the bone at desired locations of the strata of piezoelectric material. During use, when an electrical signal is applied to the strata of piezoelectric material, the strata expands and/or contracts to impart forces in a vertical direction, relative to the skull (e.g., with respect to, for example, FIG. 6B, normal to the direction of arrow 590C). Vibrational energy generated via the expansion and/or contraction is imparted into the bone. It is noted that in some embodiments, the strata may also expand and/or contract to impart forces in horizontal directions (e.g., in the direction of arrow 590C of FIG. 6B) in addition to or instead of vertical directions.

In yet another embodiment of the present invention, there is an actuator in the form of a composite component that includes a first strata and a second strata of piezoelectric material such as BTO and/or STO sandwiching a non-osseointegrated component. As detailed above, the non-osseointegrating component may be made of a material that inhibits osseointegration of that component to bone. The actuator may be placed at least partially into a recess in bone. Over time, the actuator osseointegrates to the bone at desired locations of the strata of piezoelectric material which may be established as detailed above. During use, when an electrical signal is applied to the strata of piezoelectric material, the strata expands and/or contracts to impart counter-opposing forces. That is, the strata move relative to one another away from one another. Vibrational energy generated via the expansion and/or contraction is imparted into the bone.

Figure 7:
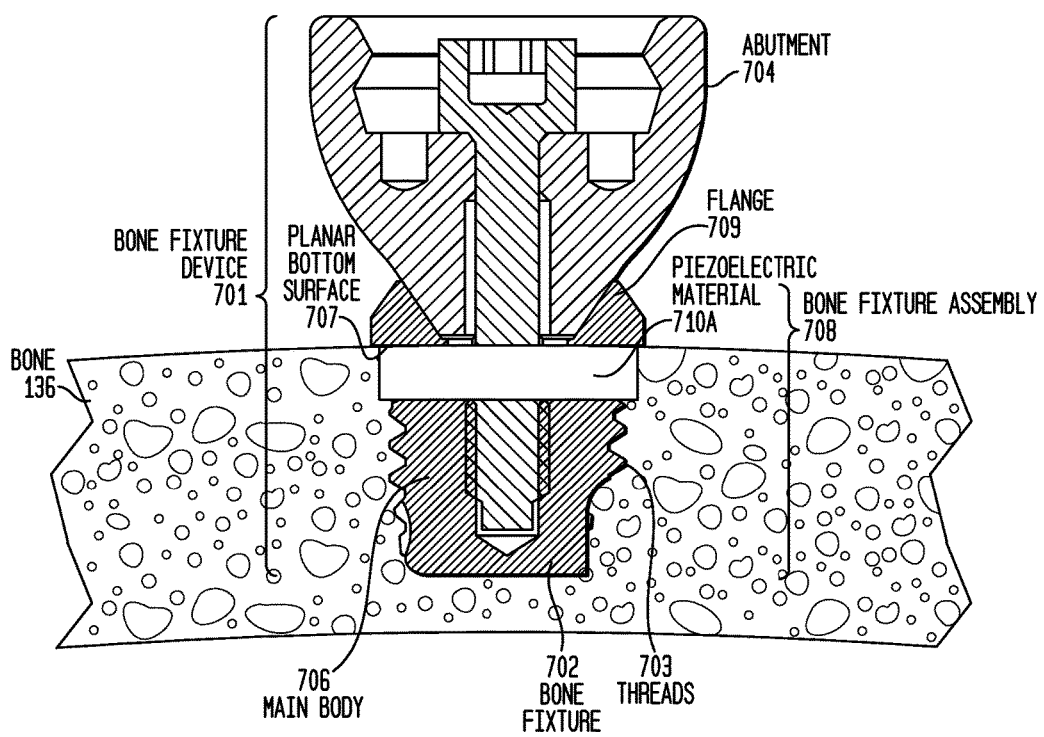
FIG. 7 is a schematic diagram presenting an exemplary embodiment of an actuator used in a combination active transcutaneous bone conduction device/percutaneous bone conduction device according to the present invention.

FIG. 7 depicts a bone fixture assembly 708 that is part of a percutaneous bone fixture device 701 according to an exemplary embodiment of the present invention. Percutaneous bone fixture device 701 includes a screw-shaped bone fixture 702 and a skin-penetrating abutment 704. Percutaneous bone fixture device 701 may be used as part of a transcutaneous bone conduction device and/or as part of a hybrid bone conduction device. By "hybrid bone conduction device," it is meant that the device has the functionality of both a percutaneous bone conduction device and a transcutaneous bone conduction device, as explained in greater detail below.

Bone fixture 702 may be made of any material that has a known ability to integrate into surrounding bone tissue (i.e., it is made of a material that exhibits acceptable osseointegration characteristics). In one embodiment, the bone fixture 702 is made of titanium. The fixture includes a main body 706 with an outer screw thread 703 which is configured to be screwed into the skull of the recipient.

The main body 706 of the bone fixture 702 may have length sufficient to securely anchor the bone fixtures into the skull without penetrating entirely through the skull. The length of the main body 706 may therefore depend on the thickness of the skull at the implantation site. In one embodiment, the main bodies of the fixtures have a length that is no greater than 5 mm, measured from the planar bottom surface 707 of the flanges 709 to the end of the distal region of the bone fixture 702 (this limits and/or prevents the possibility that the main body 706 might be screwed completely through the skull). In another embodiment, the length of the main body is from about 3.0 mm to about 5.0 mm.

The distal region of bone fixture 702 may be fitted with self-tapping cutting edges formed into the exterior surface of the fixture. Further details of the self-tapping features that may be used in some embodiments of bone fixtures used in embodiments of the present invention are described in International Patent Application WO 02/09622. In an exemplary embodiment, increased stability to the attachment between the bone fixture assembly 708 and the abutment 704 is provided as detailed in U.S. Patent Application Publication No. 2009/0082817.

Abutment 704 extends from the bone fixture 702 through muscle, fat and skin of the recipient so that a coupling apparatus of an external device may be attached thereto, as described in greater detail below.

In the exemplary embodiment, the bone fixture assembly 708 functions as an actuator, and includes a band or tube of piezoelectric material 710A (or other material that deforms when exposed to an electric signal) extending about the outer diameter of the main body 706 of the bone fixture 702. The outer diameter of the band or tube 710A may fall within the outer diameter of threads 703. Alternatively, a band or tube of piezoelectric material may extend beyond the outer diameter of threads 703, as depicted in FIG. 7. In other embodiments, the band or tube of piezoelectric material may be located so that the band or tube only contacts the surface of the bone instead of being embedded in the bone as depicted in FIG. 7 (e.g., the band or tube acts as a stop to prevent further insertion of the bone conduction device into the skull when the band or tube contacts the skull, much in the same manner that flanges 709 operate as detailed above). Functionally, the embodiment of FIG. 7 may function as an active transcutaneous bone conduction device in a similar manner to the embodiment detailed above with respect to FIG. 6C. This is because the band or tube 710A is implanted within the skull of the recipient as a result of screwing the bone fixture into the skull. Functionally, the embodiment where the band or tube of piezoelectric material is located above the skull on the surface of the skull (not shown) may function as an active transcutaneous bone conduction device in a similar manner to the embodiment detailed above with respect to FIG. 5A. This is because the band or tube is implanted above the skull of the recipient as a result of screwing the bone fixture 702 into the skull.

Electrical leads (not shown) extend from the piezoelectric material 710A through the bone fixture 702 and through the abutment 704 to an external device outside the recipient. In this regard, the bone fixture assembly 708 functionally corresponds to actuator 408 of FIG. 4 and the electrical leads that extend from the piezoelectric material 710A functionally correspond to electrical leads 454 of FIG. 4. However, instead of the electrical leads being connected to an implantable housing 454 as is detailed with respect to FIG. 4, the electrical leads are connected to an external device that may be, for example, mounted on abutment 704. The electrical leads may contain connectors that permit the electrical leads to be easily disconnected from the external device mounted on abutment 704. In some embodiments, the connectors may be quick connect-disconnect connectors that automatically connect and disconnect from the external device when the external device is mounted on abutment 704 and removed from abutment 704, respectively.

The external device used with the embodiment of FIG. 7 may include at least some of the components included in implantable housing 454 and external device 440 such that operation of the bone fixture assembly 708 as an actuator may be accomplished in a similar manner as the operation of actuator 408 of FIG. 4. That is, by extending electrical leads from the piezoelectric material 710A through the skin of the recipient to an external device, much of the functionality of the components of implantable housing 454 can be obtained by components in the external device. For example, the power source to energize the piezoelectric material may be located entirely outside the recipient. Also, some functionality of the implantable housing 454 and/or the external device 440 may no longer be needed. For example, a receiver coil need not be implanted in the recipient because percutaneous electrical leads may be used to communicate with the bone fixture assembly 708.

As noted above, embodiments consistent with that of FIG. 7 may be used in a hybrid bone conduction device. During use of such a hybrid device, an external percutaneous bone conduction device is attached to abutment 704 (or variation of abutment 704) as is, by way of example, detailed U.S. patent application Ser. No. 12/177,091 assigned to Cochlear Limited or U.S. patent application Ser. No. 12/167,796 assigned to Cochlear Limited or U.S. patent application Ser. No. 12/167,851. The percutaneous bone conduction device includes a vibratory element, such as an electromagnetic actuator and/or a piezoelectric actuator, that vibrates. Because the percutaneous bone conduction device is connected to the abutment 704, vibrations from the percutaneous bone conduction device are transferred via the abutment 704 to the bone fixture assembly 708 and then into the bone 136 in a manner analogous to the operation of a traditional percutaneous bone conduction device.

In an exemplary embodiment, the hybrid bone conduction device imparts vibrational energy to bone of the recipient via the piezoelectric material 710A and the external percutaneous bone conduction device attached to abutment 704. In some embodiments, the piezoelectric material 710A is used to generate vibrations at a lower frequency and/or a higher frequency than those generated by the external percutaneous bone conduction device, and/or visa-versa. In other embodiments, instead of or in addition to this, both the piezoelectric material 710A and the external percutaneous bone conduction device generate vibrations over frequency ranges that overlap. In yet other embodiments, in stead of or in addition to this, the piezoelectric material 710A and the external bone conduction device are used to generate vibrations during different (separate or overlapping) temporal periods. The hybrid bone conduction device may be controlled to generate vibrations from the piezoelectric material 710A and/or the external percutaneous bone conduction device in a manner that improves hearing enhancement over that which may be achieved by using only the piezoelectric material 710A or the external percutaneous bone conduction device.

It is noted that in some embodiments, the actuators detailed herein may be in the form of a circular plate or rod made from BTO and/or STO. For a maximum thickness of a plate of 30 mm, the outer diameter of the plate may be between 10 to 80 mm. For a maximum thickness of a plate of 20 mm, the outer diameter of the plate may be between 5 to 80 mm. For a maximum thickness of a plate of 10 mm, the outer diameter of the plate may be between 2 to 5 mm. For a minimum thickness of a plate of 0.15 mm, the outer diameter of the plate may be between 2 to 20 mm. For a minimum thickness of a plate of 0.3 mm, the outer diameter of the plate may be between 2 to 60 mm. For a minimum thickness of a plate of 0.5 mm, the outer diameter of the plate may be between 2 to 80 mm. Similar dimensions may be used in the case of a rod.

Also, in an exemplary embodiment, the actuator according to some embodiments herein may be in the form of a hollow tube. For a tube of a length of 1 to 70 mm having an outer diameter of less than 78 mm, the inner diameter may be less than 70 mm. For a tube of a length of 1 to 70 mm having an outer diameter of greater than 2 mm, the inner diameter may be greater than 0.8 mm. FIG. 8 details exemplary dimensions for some exemplary embodiments of an actuator in the form of a disk made from BTO and/or STO, the shaded boxes corresponding to dimensions of some embodiments.

Figure 9:
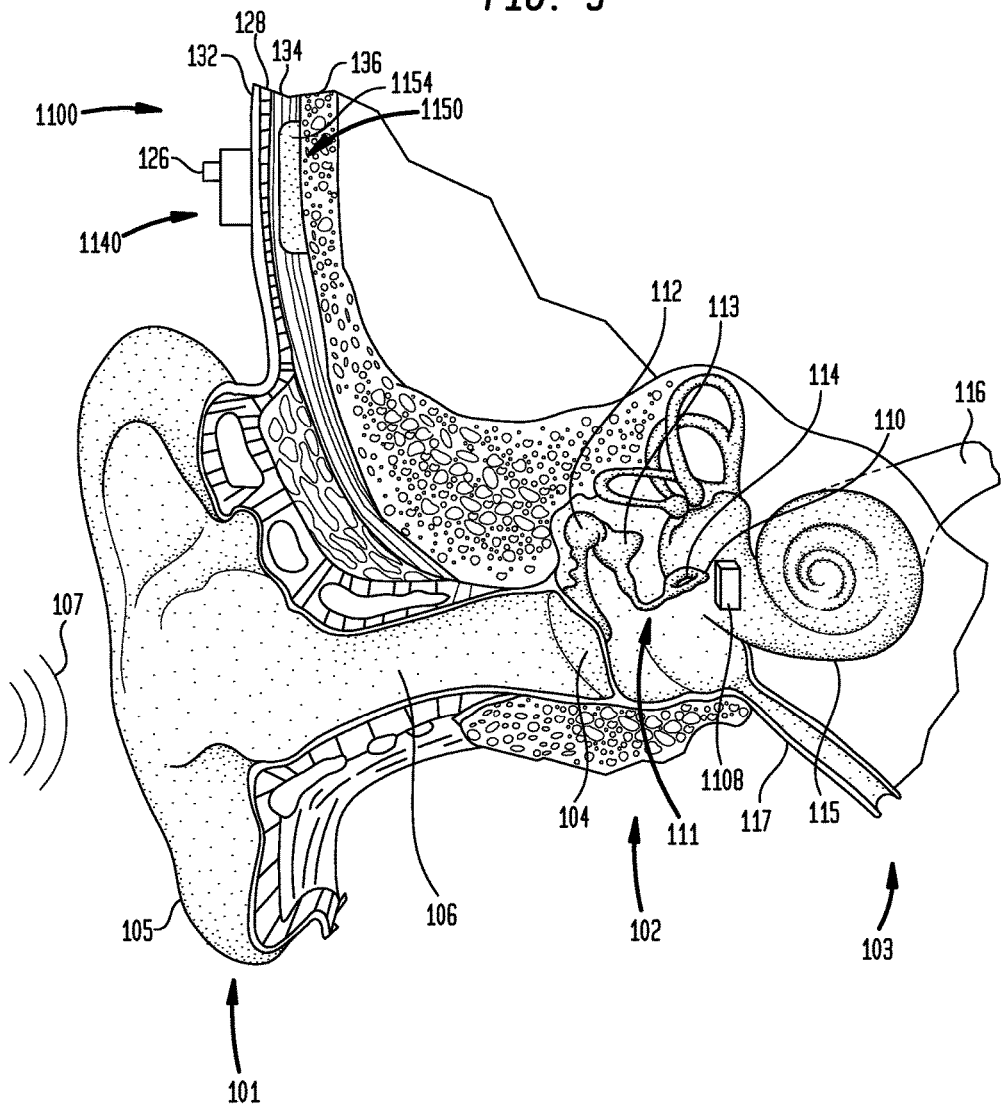
FIG. 9 is a perspective view of an exemplary middle-ear implant in which embodiments of the present invention may be implemented.

An embodiment of the present invention includes utilizing an actuator as disclosed herein and/or variations thereof to provide vibrations directly or indirectly to other parts of the anatomy of the recipient other than the skull of the recipient that will in-turn produce auditory stimulation for the recipient. For example, referring to FIG. 9, in an exemplary embodiment, there is a middle-ear hearing prosthesis 1100 including an actuator 1108 including material (e.g., BTO and/or STO) that deforms when subjected to an electrical signal according to any of the embodiments described herein and variations thereof. The deforming material of actuator 1108 is directly attached to the cochlea 115, as may be seen. In an exemplary embodiment, the deforming material of the actuator is attached to the oval or round window. The attachment may be formed by direct integration of the material of the actuator to the tissue of the oval or round window and/or through the use of a coupling implanted along with the actuator (e.g., a mechanical coupling, a biocompatible adhesive, etc.). Similar to the embodiments disclosed herein relating to a bone conduction device, the middle-ear hearing prosthesis of FIG. 9 includes an external device 1140 and an implantable component 1150. The external device 1140 functions in much the same way as one or more of the other external devices detailed above. The implantable component 1150 also functions in much the same way as one or more of the other implantable components detailed above. However, the operations of these components are tailored for use in a middle-ear hearing prosthesis (i.e., where the actuator is located in the middle-ear) as opposed to a bone conduction device (where the actuator is located on and/or in the skull), and thus the processing aspects of the system may be different. Implantable component 1150 includes a housing 1154 that includes, for example, a telecoil and other components that provide an electrical signal to actuator 1108 in a manner analogous to the components that provide electrical signals to the other actuators detailed above. Accordingly, while not shown in FIG. 9, actuator 1108 is in electrical communication with housing 1154 via, for example, electrical lead or the like. It is noted that in other embodiments, the external device 1140 and/or the housing 1154 of the implantable component may be located at other locations than that depicted in FIG. 9.

Figure 10:
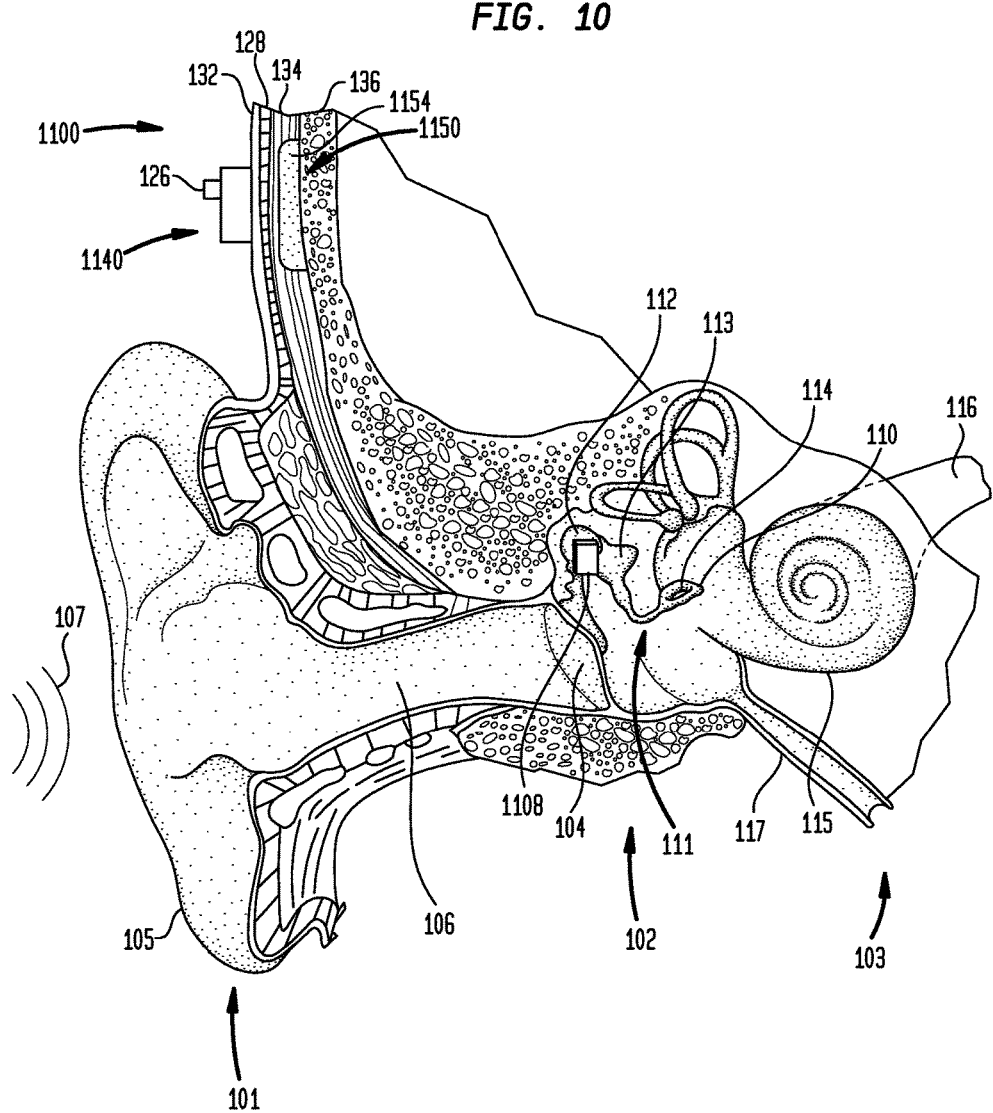
FIG. 10 is a perspective view of an exemplary middle-ear implant in which embodiments of the present invention may be implemented.

FIG. 10 depicts an alternate embodiment of a middle-ear hearing prosthesis 1100 also including an actuator 1108. The deforming material of the actuator is instead attached directly to one or more members of the ossiclular chain, as may be seen. In the embodiment of FIG. 10, the actuator 1108 is attached to the malleus 112. Actuator 1108 may be attached in the same manner or similar manner as detailed above with respect to attachment of the actuator 1108 to the cochlea.

In an alternate embodiment, an actuator having deformable material as detailed herein and/or variations thereof is located inside the cochlea. In an exemplary embodiment, the actuator provides mechanical stimulation to the hair fibers of the cochlea. In some such embodiments, the deforming material of the actuator is thus configured to be implanted inside a recipient's cochlea and configured to be mechanically coupled to the inside of the recipient's cochlea.

FIG. 11A depicts an actuator 1108A that may be used with a middle-ear hearing prosthesis. The actuator includes a housing 1112, which may be made of titanium or zinconium, including an electrical feedthrough 1114. Electrical contact pins 1116 of feedthrough 1114 permit electrical communication from the outside of the housing 1112 to the inside of the housing 1112. Leads 1118 connect the pins 1116 to an electromagnetic vibrator 1120 hermetically sealed in the housing 1112. When the electromagnetic vibrator 1120 is energized, actuator rod 1119 moves in a axial and/or a radial direction. Actuator rod 1119 is connected to one or more members of the ossicular chain or to the cochlea, thereby imparting mechanical stimulation to those components.

As just noted, the housing 1112 is hermetically sealed to protect the electromagnetic vibrator 1120 from body fluids of the recipient. In an embodiment of the present invention, as depicted in FIG. 11B, there is an actuator 1108B utilizing piezoelectric material. This embodiment is similar to that of FIG. 11A, except that the electromagnetic actuator 1120 is replaced with a piezo stack 1122 comprising a plurality of disks made of piezoelectric material stacked one on top of the other and secured together in a stack. Leads 118 connect the pins 116 of feedthrough 1114 to the piezo stack 1122. When an electrical signal is applied to the piezo stack 1122, the piezoelectric material of the stack 1122 deforms, and the actuator rod 1119, which is mechanically coupled to piezo stack 1122, moves in an axial and/or a radial direction as a result of deflection of the piezoelectric material of the piezo stack 1122. In a middle-ear implant utilizing actuator 1108B, actuator rod 1119 is connected to one or more members of the ossicular chain or to the cochlea.

If the piezo stack 1122 is made from biocompatible material such as BTO, such as the embodiment depicted in FIG. 11B, the housing 1112 need not hermetically seal the piezo stack 1122 from the body fluids of the recipient, in contrast to the housing 1112 of actuator 1108A. Accordingly, the housing 1112 serves only to protect the piezo stack 1122 from physical damage resulting from applied force. Alternatively or in addition to this, the housing 1112 may provide structural support to the components of the actuator 1108B, such as supporting the feedthrough 1114 above the piezo stack 1122 as shown.

FIG. 11C depicts an actuator 1108C that utilizes a piezo stack 1124 that substantially conforms to piezo stack 1122 of FIG. 11B, and also utilizes piezoelectric material that is biocompatible. However, actuator 1108C does not utilize a housing 1112 to protect that piezo stack 1122. Instead, the piezo stack 1124 is directly attached to one or more members of the ossicular chain or to the cochlea. Because there is no housing, a feedthrough is not necessary. Instead, an electrical contact pin support 1126 supports electrical contact pins 1128. Pins 1128 conduct electricity to the piezoelectric material of the piezo stack 1124. Upon application of an electrical signal to the piezo stack 1124, the piezoelectric material of the piezo stack 1124 deforms, thereby imparting vibrations to the recipient's middle ear.

It is noted that in some embodiments of the present invention, actuators 1108B and/or 1108C may be connected to the skull to transmit vibrations to the skull.

Figure 12:
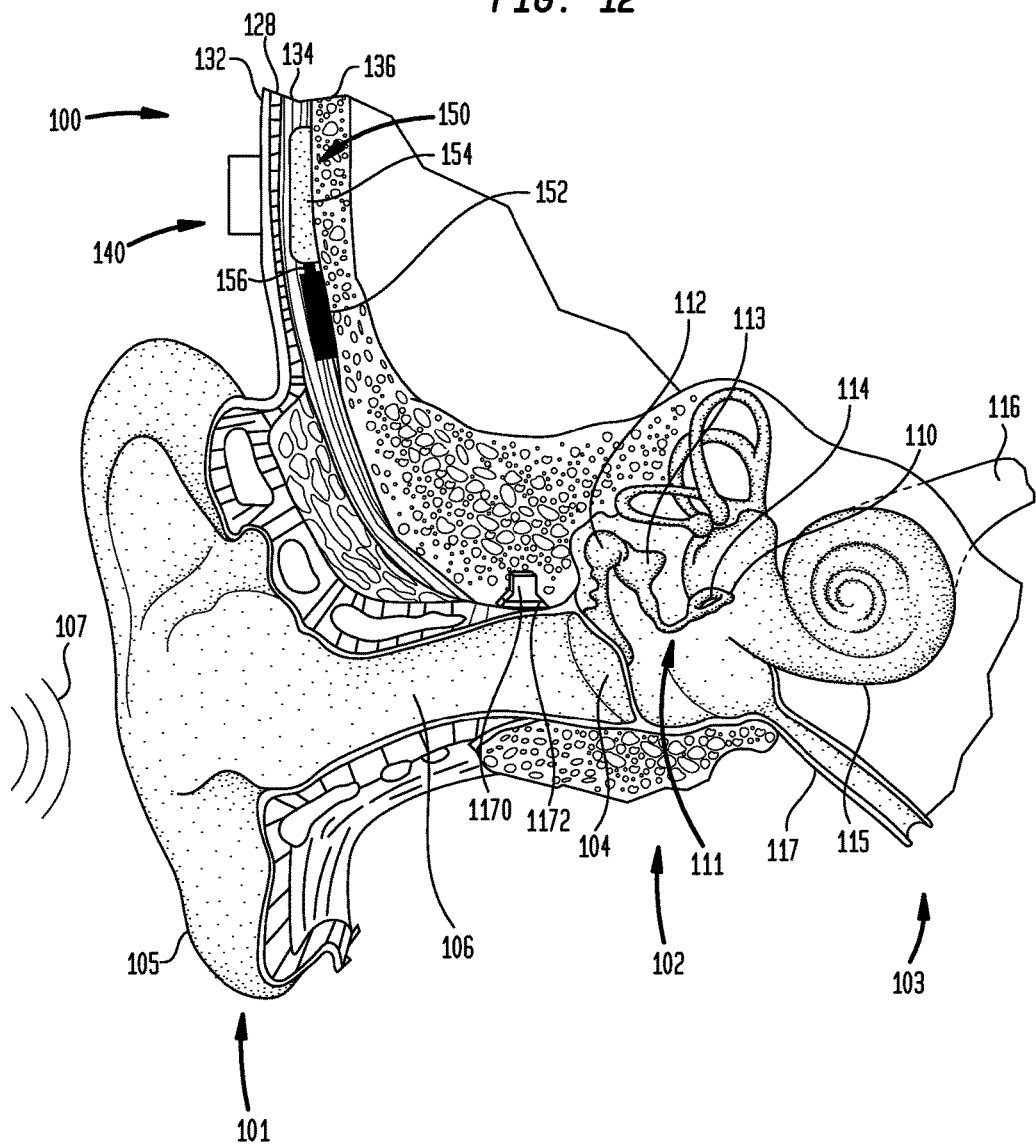
FIG. 12 is a perspective view of a hearing prosthesis utilizing an implantable microphone according to an embodiment of the present invention.

In yet another alternate embodiment, piezoelectric material implanted in the recipient is a utilized as a transducer. In an exemplary embodiment, it is used as part of a sound capture device such as an implantable microphone. By way of example, referring to FIG. 12, which is identical to FIG. 1 detailed above except for the absence of sound capture device 126 and the addition of implanted microphone 1170 (the details of which will be provided below), the sound wave 107, being a wave that diffuses as it travels through the atmosphere, also impinges upon the outer skin 132 of the recipient. Energy from that impinging sound wave travels through the skin to the implanted piezoelectric material 1172 of the implanted microphone 1170. This energy deforms the piezoelectric material (typically compressing the piezoelectric material resulting from the pressure applied to the material), causing the piezoelectric material to generate an electrical charge in response to this deformation. While not shown in FIG. 12, the piezoelectric material is in electrical communication with an implanted sound processor of implantable component 150 that receives electrical signals from the piezoelectric material resulting from the generated electrical charge in a manner that may be analogous to how a sound processor receives electrical signals from a conventional microphone. The sound processor processes those signals in a manner that may be analogous to how the sound processor processes the electrical signals from a conventional microphone. It is noted that there may be one or more intermediate components between the piezoelectric material and the sound processor, as is detailed above, for example, with respect to intermediate components between a microphone and a sound processor. In some such alternate embodiments, this permits a fully implantable hearing prosthesis to be provided to a recipient in a manner analogous to such systems utilizing conventional implanted microphones.

Figure 13:
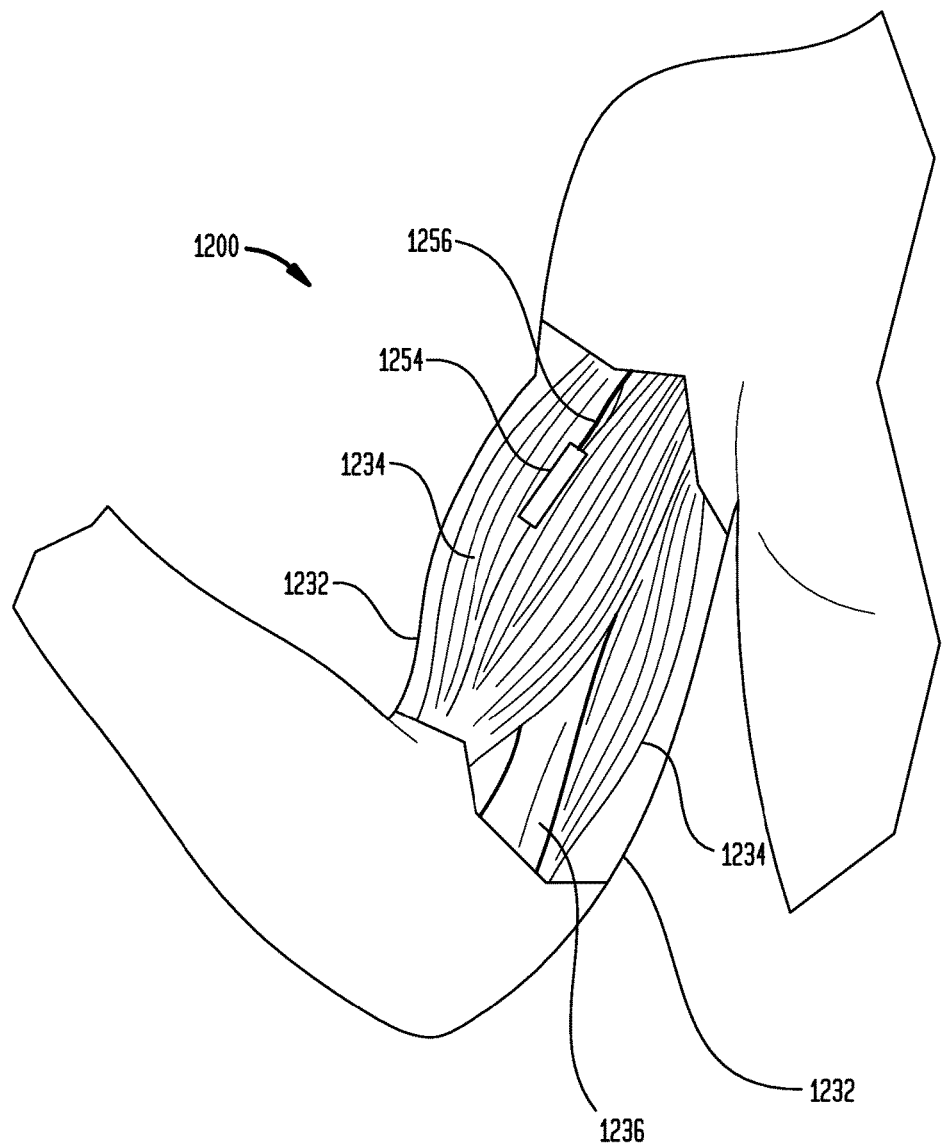
FIG. 13 is a perspective view of an implantable electricity generator according to an embodiment of the present invention.

In yet another alternate embodiment, the transducer made from piezoelectric material implanted in the recipient is an implantable electricity generator. That is, the piezoelectric material is used to generate electricity to power implanted electrical components or to charge a power storage device, such as a battery. In an exemplary embodiment, the piezoelectric material is implanted beneath the skin of the recipient in such a manner that pressure may be repeatedly applied to the material through the skin. In alternate embodiments, pressure may be applied via the use of muscles. For example, referring to FIG. 13, which depicts an arm 1200 of a recipient, piezoelectric material 1254 is implanted in the recipient between bone 1236 and skin 1232. More specifically, piezoelectric material 1254 is implanted between biceps 1234 such that when the biceps 1234 are used during the normal course of events, pressure is applied to the piezoelectric material 1254. This pressure causes the piezoelectric material 1254 to deform, thereby generating electricity. That is, because the piezoelectric material 1254 is positioned adjacent to muscle tissue such that it deforms in response to contraction of the muscle tissue, the piezoelectric material 1254 generates electricity as a result of the normal use of the recipient's arm. The piezoelectric material is in electrical communication via electrical leads 1256 with an implanted power storage device, such as a battery, and/or any other implanted component that is powered by electricity, such as any one or more of the components detailed herein (not shown in FIG. 13). Further by example, piezoelectric material 1254 maybe implanted between or against leg muscles, etc., or any other muscle that will permit the piezoelectric material to generate electricity that may be usefully harnessed.

In some embodiments of the present invention, the piezoelectric material is directly attached to muscle tissue by direct integration of the material of the muscle tissue and/or through the use of a coupling implanted along with the piezoelectric material (e.g., a mechanical coupling, a biocompatible adhesive, etc.). In some embodiments, the piezoelectric material may be formed in a manner that it surrounds some or all of the muscle tissue such that a separate connector or bond is not needed. In other embodiments, the material may be positioned such that it is trapped between muscle tissue and or other tissue such that it will not effectively move from a desired location, also alleviating the need for a separate connector or bond.

In an exemplary embodiment, the implantable microphone system detailed above that also utilizes implanted piezoelectric material is also used to generate electricity, or, more specifically, the electricity that is generated by the implantable microphone is harnessed in a manner beyond using the electricity to carry a sound signal to a signal processor (e.g., is used to charge a battery). In some embodiments, the hearing prosthesis utilizing the implanted microphone system is configured to switch between the functionality of an implantable microphone and a power generation device. This switch to a power generation device may be done, for example, when a recipient does not need to use the hearing prosthesis to hear.

An embodiment of the present invention also includes utilizing the implanted piezoelectric material to generate an electrical charge thereon. This generated electrical charge is used to enhance osseointegration of the piezoelectric material to bone. By way of example, the recipient or caregiver may massage his or her skin at a location adjacent the implanted piezoelectric material, thereby deforming the implanted piezoelectric material such that an electrical charge may be established therein. To facilitate this, the bone conduction device may configured such that is may be switched (either manually or automatically) to a mode that ensures that the electrical leads to the piezoelectric material or other pertinent electrical connection do not conduct the electrical charge from the material.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A hearing prosthesis comprising:
   an actuator including a material that deforms in response to an electrical signal directly applied to the material and that is adapted to, upon implantation in a recipient, transmit vibrations representative of a sound signal to an organ of the recipient, wherein the material is configured to be at least partially directly exposed to at least one of body tissue or fluid of the recipient, wherein at least one of:
   (i) the actuator is adapted to be implanted such that the material directly contacts the skull of the recipient;
   (ii) the material is a material that enhances osseointegration;
   (iii) the hearing prosthesis is an active transcutaneous bone conduction device; or
   (iv) the actuator is configured to be implanted inside a cochlea of the recipient and configured to be mechanically coupled to the inside of the cochlea.

2. The hearing prosthesis of claim 1, wherein the material is substantially devoid of lead zirconate titanate.

3. The hearing prosthesis of claim 1, wherein the material is doped with a second material that enhances osseointegration of the material with the skull of the recipient.

4. The hearing prosthesis of claim 1, wherein the actuator is adapted to be implanted such that the material directly contacts the skull of the recipient.

5. The hearing prosthesis of claim 1, wherein the actuator includes:
   a first surface formed by the material, the first surface being adapted to directly contact the skull of the recipient, the first surface having a first surface roughness; and
   a second surface formed by the material located away from the first surface, the second surface having a second surface roughness, the first surface roughness being more rough than the second surface roughness.

6. The hearing prosthesis of claim 5, wherein the first surface roughness is significantly more rough than the second surface roughness such that the first surface roughness accelerates the osseointegration of the actuator to the skull at the first surface relative to that which would take place if the first surface had the second surface roughness.

7. The hearing prosthesis of claim 1, wherein the material is a material that enhances osseointegration.

8. The hearing prosthesis of claim 1, wherein the hearing prosthesis is an active transcutaneous bone conduction device.

9. The hearing prosthesis of claim 1, wherein the hearing prosthesis comprises a percutaneous bone fixture device including a bone fixture and a skin-penetrating abutment, and wherein the actuator is attached to the bone fixture.

10. The hearing prosthesis of claim 1, wherein the hearing prosthesis comprises a bone fixture, wherein the actuator is attached to the bone fixture.

11. The hearing prosthesis of claim 1, wherein the hearing prosthesis comprises a percutaneous bone fixture device including a bone fixture, a skin-penetrating abutment, and a second actuator mounted to the abutment such that, in use, the second actuator is located outside the recipient, and wherein the actuator is attached to the bone fixture such that, in use, the actuator is located in the recipient.

12. The hearing prosthesis of claim 1, wherein:
the material is configured to be in direct contact with bone of the recipient.

13. The hearing prosthesis of claim 1, wherein the material is a first material, the hearing prosthesis further comprising:
a second material that is dimensionally stable in response to the electric signal, the second material being distinct from the first material and directly contacting the first material, wherein the second material is configured to be directly attached to a bone of the recipient so as to provide a complete barrier between the first material and the bone.

14. The hearing prosthesis of claim 1, wherein the material is a first material, the hearing prosthesis further comprising:
a second material that does not deform in response to the electric signal, the second material being distinct from the first material and directly contacting the first material, wherein the second material is configured to be directly attached to a bone of the recipient so as to provide a complete barrier between the first material and the bone.

15. The hearing prosthesis of claim 1, wherein the actuator is configured to be implanted inside the cochlea of the recipient and configured to be mechanically coupled to the inside of the cochlea.

16. A transducer, comprising:
a material that at least generates electricity when deformed, wherein the material is adapted to be at least partially exposed to at least one of body tissue or fluid of the recipient, wherein the material is a material that enhances osseointegration.

17. The transducer of claim 16, wherein the transducer is an implantable electricity generator, and wherein the material is adapted to be positioned adjacent to muscle tissue and deform in response to contraction of the muscle tissue.

18. The transducer of claim 17, wherein the transducer is in electrical communication with a power storage device.

19. The transducer of claim 16, wherein:
the transducer is a transducer of a middle ear hearing prosthesis configured such that, in use, the material is in direct contact with at least one of an ossicle of a recipient or a cochlea of the recipient.

20. The transducer of claim 16, wherein:
the transducer is an actuator of a middle ear hearing prosthesis configured such that the material deforms when exposed to electricity so as to drive the prosthesis and thus evoke a hearing percept.

21. The transducer of claim 16, wherein the material includes barium titanate.

22. The transducer of claim 16, wherein the material is strontium titanate.

23. A method of imparting vibrational energy to bone, the method comprising:
deforming a deformable material in response to an electric signal applied thereto which results in a transduction by the material of electricity into the deformation; and
imparting vibrational energy resulting from the deformation of the deformable material directly from the deformable material to the bone, wherein
the bone is a skull of the recipient.

24. The method of claim 23, wherein:
the deformable material is at least partially embedded in a recess surgically cut into a skull of a recipient; and
the deformation of the deformable material imparts at least one of tensile or compressive forces onto sidewalls of the recess.

25. The method of claim 23, wherein the material is osseointegrated to the bone.

* * * * *